United States Patent [19]
Li et al.

[11] Patent Number: 5,693,756
[45] Date of Patent: Dec. 2, 1997

[54] AMILORIDE-SENSITIVE SODIUM CHANNEL AND METHOD OF IDENTIFYING SUBSTANCES WHICH STIMULATE OR BLOCK SALTY TASTE PERCEPTION

[75] Inventors: Xiao-Jiang Li; Seth Blackshaw; Solomon H. Snyder, all of Baltimore, Md.

[73] Assignee: The Johns Hopkins University, Baltimore, Md.

[21] Appl. No.: 376,362

[22] Filed: Jan. 23, 1995

Related U.S. Application Data

[63] Continuation-in-part of Ser. No. 202,654, Feb. 28, 1994, abandoned.

[51] Int. Cl.$^6$ ............................................. C07K 14/47
[52] U.S. Cl. ............................................. 530/350; 436/501
[58] Field of Search ............................................. 530/350

[56] References Cited

PUBLICATIONS

Li et al., "Expression and Localization of Amiloride-Sensitive Sodium Channel Indicate a Role for Non-Taste Cells in Taste Perception", *Proc. Natl. Acad. Sci. USA* 91:1814–1818 (1994).

Gilbertson et al., "Proton Currents Through Amiloride-Sensitive Na$^+$ Channels in Isolated Hamster Taste Cells: Enhancement by Vasopressin and cAMP", *Neuron* 10:931–942 (1993).

McCutcheon, "Human Psychophysical Studies of Saltiness Suppression by Amiloride", *Physiology & Bahavior* 51:1069–1074 (1992).

Desor et al., "Effects of Amiloride on Salt Taste in Humans", *Chemical Senses* 14(6):793–803 (1989).

Gilbertson et al., "Proton Currents Through Amiloride-Sensitive Na Channels in Hamster Taste Cells", *J. Gen. Physiol.* 100:803–824 (1992).

Heck et al., "Salt Taste Transduction Occurs Through an Amiloride-Sensitive Sodium Transport Pathway", *Science* 223:403–405 (1984).

Avenet et al., "Amiloride-Blockable Sodium Currents in Isolated Taste Receptor Cells", *J. Membrane Biol.* 105:245–255 (1988).

Palmer et al., "Amiloride-Sensitive Na Channels From the Apical Membrane of the Rat Cortical Collecting Tubule", *Proc. Natl. Acad. Sci. USA* 83:2767–2770 (1986).

Schiffman et al., "Amiloride Reduces the Taste Intensity of Na$^+$ and Li$^+$ Salts and Sweeteners", *Proc. Natl. Acad. Sci. USA* 80:6136–6140 (1983).

Canessa et al., "Epithelial Sodium Channel Related to Proteins Involved in Neurodegeneration", *Nature* 361:467–470 (1993).

Lingueglia et al., "Expression Cloning of an Epithelial Amiloride-Sensitive Na$^+$ Channel", *FEBS* 318(1):95–99 (1993).

Li et al., Mol. Pharmacol. 47:1133–1140 (1995).
Canessa et al., Nature 367:463–467 (1994).

*Primary Examiner*—Robert A. Wax
*Assistant Examiner*—Eric Grimes
*Attorney, Agent, or Firm*—Banner & Witcoff, Ltd.

[57] ABSTRACT

An amiloride sensitive sodium channel (ENAC) has been localized to the epithelium of tongue, including taste tissue. This discovery provides a method of identifying substances which stimulate or block salty taste in mammals. Alternatively spliced forms have also been identified.

2 Claims, 17 Drawing Sheets

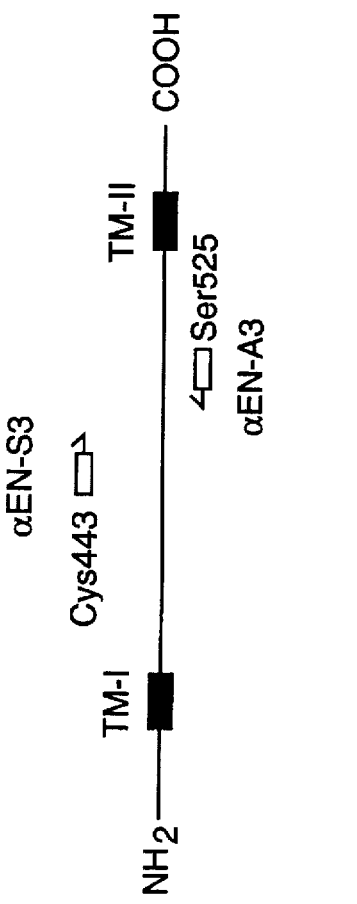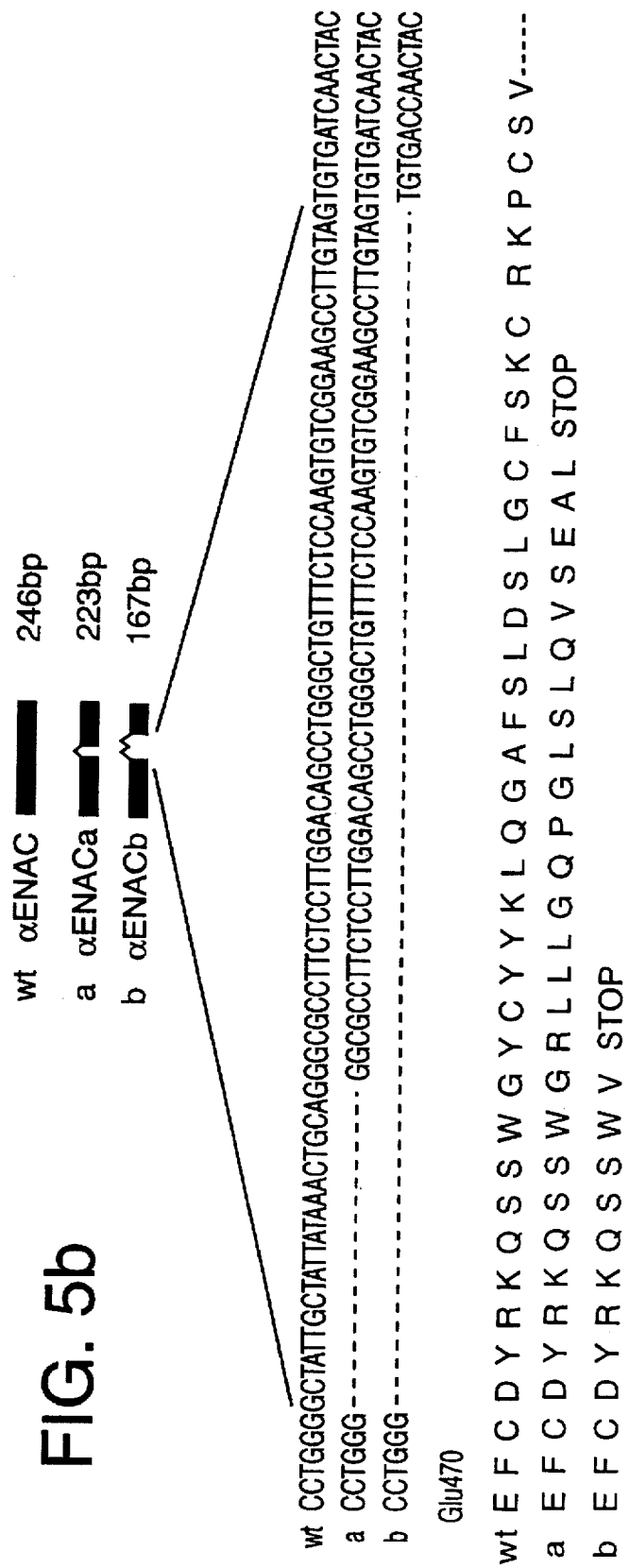
FIG. 5a
FIG. 5b

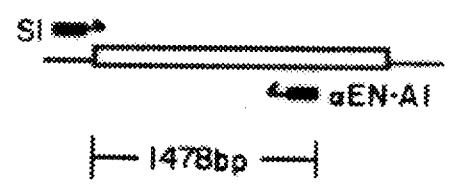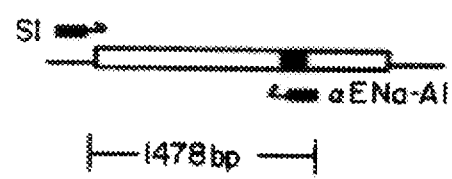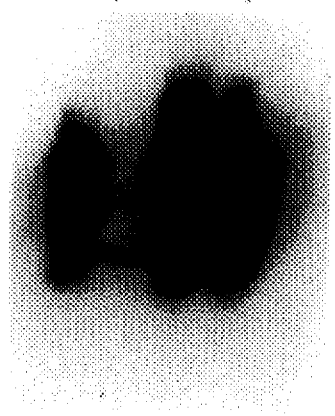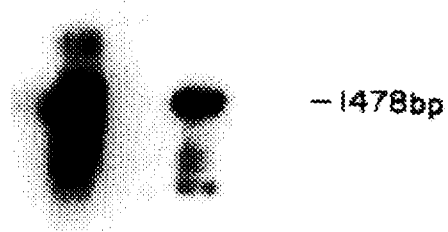
FIG. 6C
FIG. 6D

AMILORIDE-SENSITIVE SODIUM CHANNEL AND METHOD OF IDENTIFYING SUBSTANCES WHICH STIMULATE OR BLOCK SALTY TASTE PERCEPTION

This application is a continuation-in-part of application Ser. No. 08/202,654, filed Feb. 28, 1994, now abandoned.

FIELD OF INVENTION

The invention relates to an amiloride-sensitive sodium channel which has been found to regulate the response of taste cells to salt. The invention also relates to a method for screening substances to identify agents which stimulate salty taste as well as agents which block salty taste.

BACKGROUND OF THE INVENTION

Unlike other central modalities, taste utilizes a diversity of signal transduction mechanisms. Sweet taste (Striem et al., 1989, *Biochem. J.*, 260: 121–126; Tonosaki et al., 1988, *Nature*, 331:354–356) and bitter taste (Akabas et al., 1988, *Science*, 242:1047–1050; Hwang et al., 1990, *Proc. Natl. Acad. Sci. USA*, 87:7395–7399) appear to involve G protein-linked receptors. Sour taste is mediated by a proton channel (Gilbertson et al., 1993, *Neuron*, 10:931–942; Gilbertson et al., 1992, *J. Gen. Physiol.*, 100:803–824) and possibly blockade of voltage-gated potassium channels (Kinnamon et al., 1988, *Proc. Natl. Acad. Sci. USA*, 85:7023–7027). The salty task of sodium requires a sodium channel (Heck et al., 1984, *Science*, 223:403–405; Avenet et al., 1988, *J. Membrane Biol.*, 105:245–255).

Active sodium reabsorption by epithelia throughout the body, including kidney tubules, the distal colon, sweat and salivary glands is mediated by amiloride-sensitive epithelial sodium channels (Garty and Benos, 1988, *Physiol. Rev.*, 68:309–372). Salty task also appears to involve an amiloride-sensitive sodium channel. Amiloride inhibits salty task perception both in animals and humans (Heck et al., 1984, *Science*, 223:403–405; Avenet and Lindemann, 1988, *J. Membrane Biol.*, 105:245–255; Schiffman et at., 1983, *Proc. Natl. Acad. Sci. USA*, 80:6136–6140). Amiloride-sensitive channels may also modulate sour taste, which is diminished by amiloride (Gilbertson et al., 1992, *J. Gen. Physiol.*, 100:803–824). Amiloride(N-amidino-3,5-diamino-6-chloropyrazine carboxamide) acts at specific receptor sites in the kidney to block sodium reabsorption (Palmer et al., 1986, *Proc. Natl. Acad. Sci. USA*, 83:2767–2770).

An amiloride-sensitive sodium channel has been purified from kidney as a large protein complex of about 730 kD, which comprises several subunits (Benos et al., 1987, *J. Biol. Chem.*, 262:10613–10618; Benos et al., 1986, *Proc. Natl. Acad. Sci. USA*, 83:8525–8529). Different cDNAs for subunits of the amiloride-sensitive sodium channel have been cloned, but the expressed proteins did not confer sodium channel activity (Barbry et al., 1990, *Proc. Natl. Acad. Sci. USA*, 87:7347–7351; Staub et al., 1992, *J. Cell Biol.*, 119:1497–1506). More recently, the alpha subunit of the amiloride-sodium channel has been cloned and shown to confer amiloride-sensitive sodium activity. Canessa et al. (*Nature*, 1993, 361:467–470) and Lingueglia et al. (*FEBS Lett*, 1993, 318:95–99) cloned the alpha subunit of a rat colon amiloride-sensitive sodium channel of about 70 kD which confers sodium channel activity; it is sensitive to amiloride and various derivatives in proportion to their pharmacologic activity.

The identity of an amiloride-sensitive sodium channel having a role in salty taste perception has not previously been determined. There is a need in the art for the identification of such sodium channels in order to provide a means to develop reagents targeted to enhance or inhibit salty taste perception.

SUMMARY OF THE INVENTION

A cloned subunit ($\alpha$subunit) of the amiloride-sensitive salt channel has now been discovered to be localized to the tongue, including taste tissue, and has been identified as having a role in salty taste perception. Alternatively spliced forms, which are similarly localized, have also been discovered. These discoveries provide the art with tools for identifying salt substitutes and salt antagonists.

It is an object of the invention to provide a method for screening substances to identify those which enhance salty taste.

It is another object of the invention to provide a method for screening substances to identify those which block perception of a salty taste.

These and other objects are provided by one or more of the following embodiments.

The invention provides products of alternative splicing of $\alpha$ENAC, called $\alpha$ENACa and $\alpha$ENACb. Isolated cDNA and proteins of $\alpha$ENACa and $\alpha$ENACb are provided as described in FIG. 5. The cDNA and protein for $\alpha$ENACa and $\alpha$ENACb are identical to native $\alpha$ENAC except for the changes indicated in FIG. 5.

Transfected host cells and recombinantly produced protein are also contemplated by the invention.

Synthetically produced liposomes which contain at least one of the amiloride-sensitive sodium channels described herein also form part of the invention.

Another embodiment of the invention is a method for screening substances to identify those which stimulate or block perception of a salty taste. The method comprises the steps of:

providing a membrane containing an amiloride-sensitive sodium channel;

applying a test substance and a salty-tasting substance to one side of said membrane; and determining whether the test substance stimulates or inhibits transport of the salty-tasting substance across the membrane. A test substance which inhibits transport of the salty tasting substance across the membrane is identified as a substance which will block perception of a salty taste. A test substance which stimulates transport of the salty-tasting substance across the membrane is identified as a substance which will enhance perception of a salty taste.

In still another embodiment of the invention a method is provided for screening substances to identify those which stimulate or block perception of a salty taste. The method comprises the steps of:

providing an amiloride sensitive salt channel comprising an amiloride-sensitive sodium channel peptide;

applying a test substance and a labeled amiloride or derivative thereof; and determining whether the test substance prevents labeled amiloride or derivative thereof from binding to the peptide, test substances which prevent said binding to the amiloride-sensitive sodium channel peptide being identified as substances which will stimulate or block perception of a salty taste.

Substances which stimulate the perception of a salty taste find use, for example, as salt substitutes. Salty taste antagonists can be used, for example, to mask undesirable salty tastes in foods and medicines.

BRIEF DESCRIPTION OF THE DRAWINGS

FIGS. 3A-1 through 3A-4 and 3B-1 through 3B-6 show localization of αENAC mRNA in rat tongue epithelium.

FIGS. 4A-1 through 4A-4 and 4B-1 through 4B-4 show in situ hybridization of αENAC mRNA in peripheral tissues.

FIG. 5A illustrates identification of alternatively spliced transcripts from rat taste tissues by RT-PCR using degenerate sense and antisense oligonucleotides.

FIG. 5B shows nucleotide and amino acid sequence comparisons of published native αENAC and alternatively spliced forms αENACa and αENACb. The nucleotide sequences of native αENAC, αENACa, and αENACb are also shown in SEQ ID NOS. 14, 15, and 16, respectively. The amino acid sequences of native αENAC, αENACa, and αENACb are also shown in SEQ ID NOS: 17, 18, and 19, respectively.

FIG. 6A-6D show RT-PCR analysis of RNA expression of native αENAC and the alternatively spliced form αENACa.

FIG. 9B-1 and 9B-2 show saturation analysis of [$^3$H] phenamil binding to transfected cells.

DETAILED DESCRIPTION OF THE INVENTION

Molecular cloning studies have revealed that the alpha subunit of the amiloride-sensitive epithelial sodium channel (ASSC or ENAC for epithelial Na channel) confers channel activity. The expression of this alpha subunit of ENAC (αENAC) in various tissues corresponds to the presence of amiloride-sensitive sodium channel activity. Messenger RNA corresponding to a cloned αENAC has been localized to the tongue, including taste tissue, and identified as having a role in taste perception. Two alternatively spliced transcripts of αENAC (αENACa and αENACb) have also been discovered.

Figures 1, 3A:
Figures 2, 3A:
Figures 3, 3A:
Figures 3, 3A, 4:
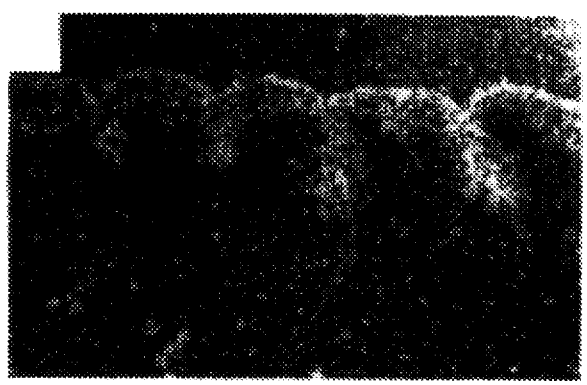
Figures 1, 3B:
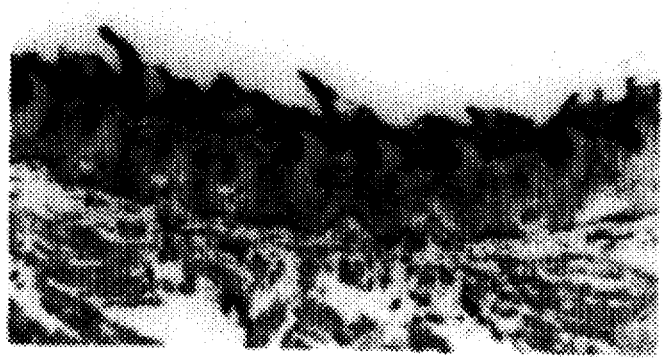
Figures 2, 3B:
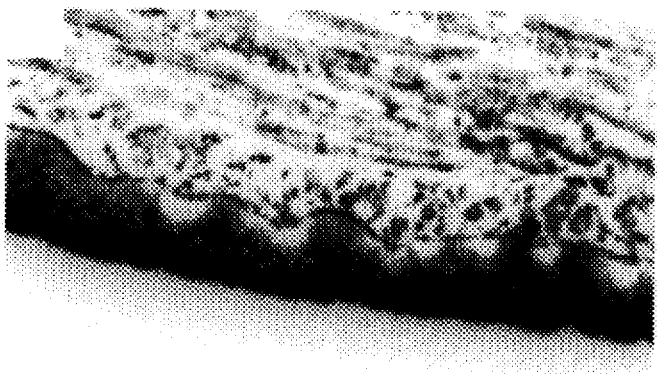
Figures 3, 3B:
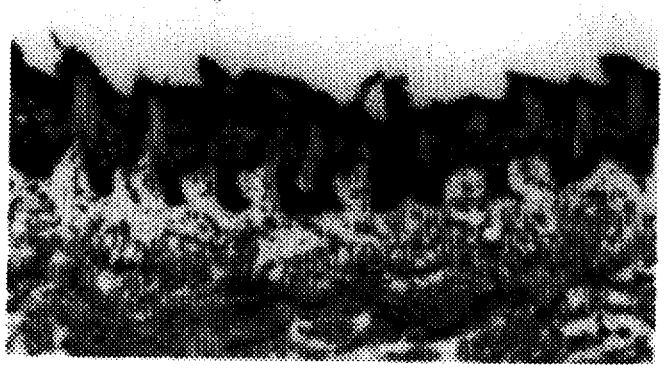
Figures 3, 3B, 4:
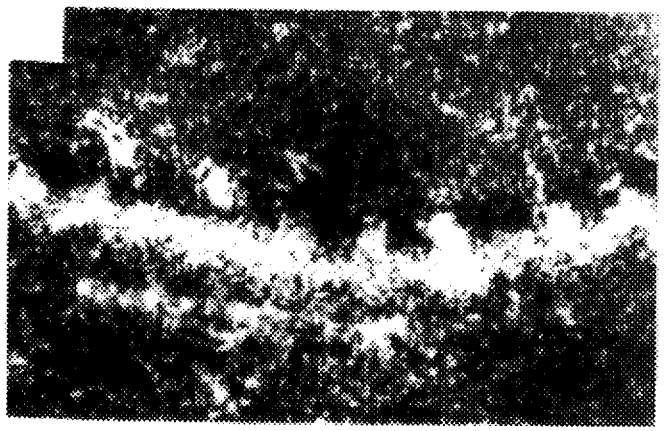
Figures 3, 3B, 4, 5:
Figures 3, 3B, 4, 5, 6:
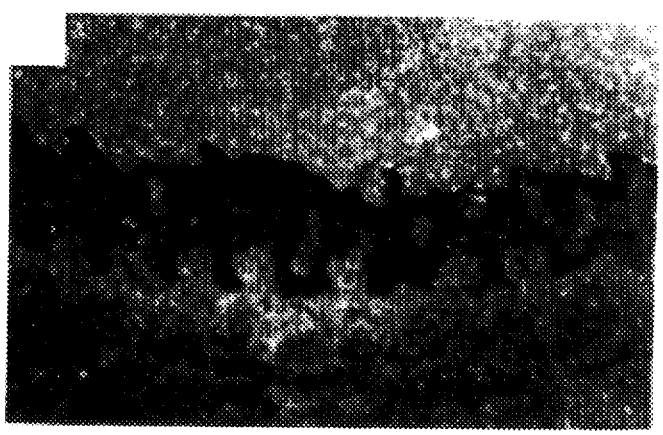
Figures 1, 4A:
Figures 2, 4A:
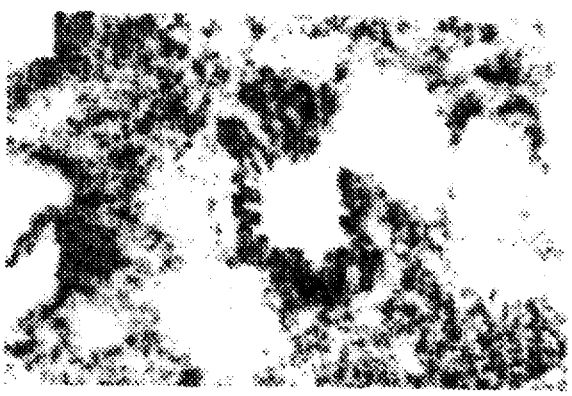
Figures 3, 4A:
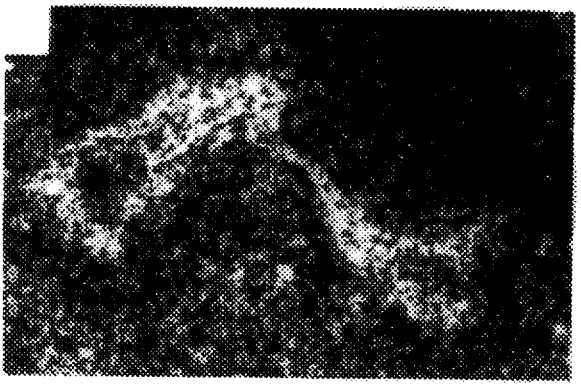
Figures 4, 4A:
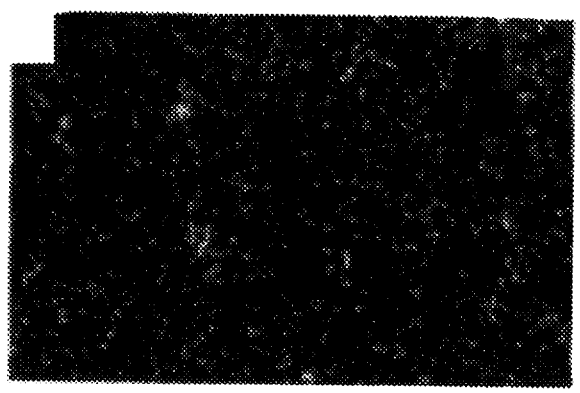
Figures 1, 4B:
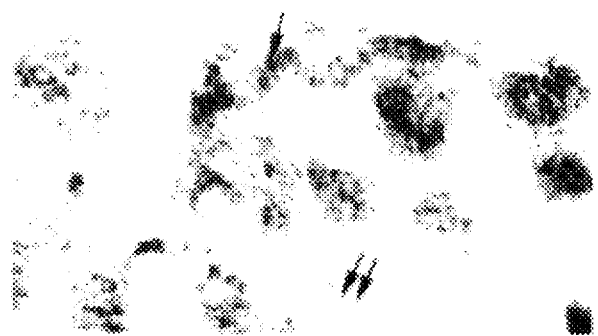
Figures 2, 4B:
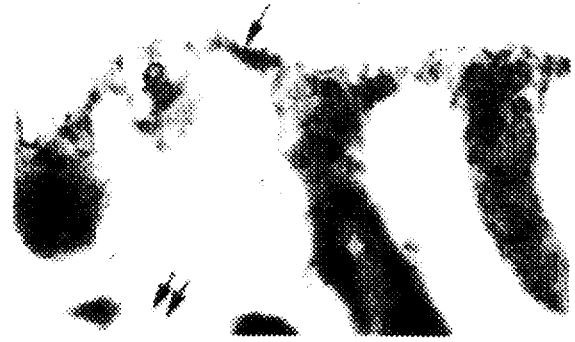
Figures 3, 4B:
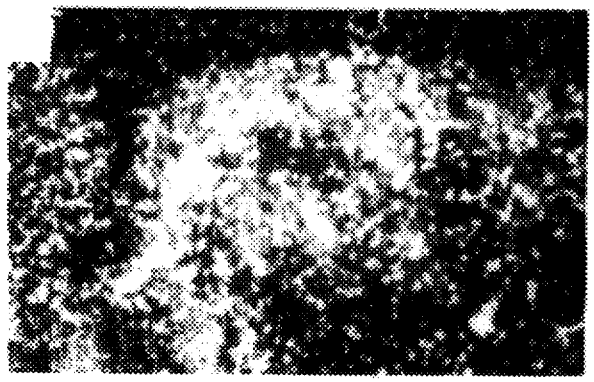
Figures 4, 4B:
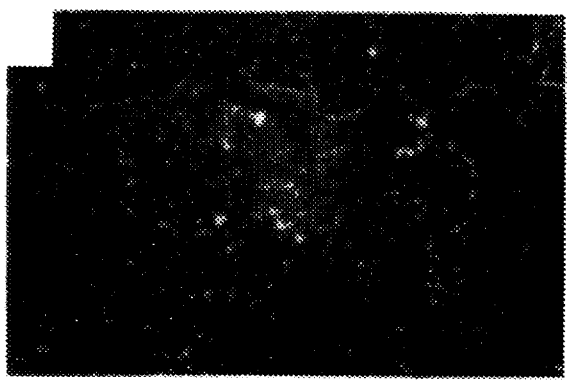

In accordance with one aspect of the invention, a cell is transfected with a nucleotide sequence which encodes αENAC. Such sequences are known in the art (Canessa et al, 1993, *Nature*, 361:467–470; Lingueglia et al., 1993, *FEBS Lett.*, 318:95–99, the entire disclosures of which are hereby incorporated by reference). An alternatively spliced sequence, as described herein, may also be used. cDNA encoding spliced forms αENACa and αENACb are shown in FIG. 5, to the extent that they differ from native αENAC. Upon expression of the sequence, αENAC is synthesized and inserted into the cell membrane. Stable or transient transfectants can be used. Means for preparing and selecting transfected cells are well known in the art.

Transfectants as described can be used to assay a test substance's ability to stimulate or inhibit ENAC-mediated transport of sodium ions or other ENAC substrates. Transport of salty substances into transfected cells is determined and compared to non-transfected control cells. Transport of labeled substances across the cell membrane can be measured. For example, the function of the channel can be measured biochemically by the passage of radioactive sodium or other related ions such as lithium. Alternatively, the electrical conductance or osmotic pressure across the cell membrane can be determined, both of which would reflect the transport of substances across the cell membrane. Transport, as used herein, means the increased ability of substances to traverse the membrane via ENACs. Candidate salt substitutes or enhancers are agents that enhance transport while candidate antagonists would be agents that block such transport. Means for measuring both electrical conductance and osmotic pressure are well known in the art. See, for example, Leonard et al., 1992, *Proc. Natl. Acad. Sci. USA*, 89:10094–10098 and Lipton et al., 1987, *J. Physiology*, 385:361–391.

In addition to using transfected cells to monitor channel activity, channel activity can be monitored in frog oocytes transfected with RNA encoding the channel protein. Xenopus oocytes express very limited endogenous sodium channel activity. ENAC can also be reconstituted in liposomes. Reconstitution of purified amiloride-sensitive salt channels into membranes composed of lipids is particularly advantageous since such a proteoliposome system enables the evaluation of test substances without the potentially confounding effects of other membrane proteins. The use of liposome membranes, therefore, provides the art with a method of unambiguously identifying potentially useful agents. Black lipid membranes may also be used.

Given the published sequences of native αENAC and the altered portions of αENACa and αENACb, one of ordinary skill in the art can readily produce isolated cDNA molecules or proteins containing the sequences of the altered forms. These can be conveniently produced by recombinant DNA technology. Isolated cDNA molecules are typically purified away from other molecules in a cDNA library. Isolated protein is typically purified to some extent so that it comprises a significant portion of the proteins present in a preparation. Isolated protein is often purified from other cellular components, as well, such as DNA, RNA, lipids, etc.

Construction of a Rat Circumvallate Papillae cDNA Library

Circumvallate papillae containing tongue epithelium and taste buds were dissected as described in Hwang et al., *Proc. Natl. Acad. Sci. USA*, 1990, 87:7395–7399, and RNA extracted from the circumvallate papillae of 500 rats. Poly (A$^+$) RNA was prepared by passing RNA through an oligo dT column twice. About 5 µg poly(A$^+$) RNA were converted to cDNA for construction of the cDNA library, using the Lambda zap vector cDNA library synthesis Kit (Stratagene). 1.5 million independent recombinants with an average insert size of 1.2 kb were obtained.

Tissue Distribution of ASSC mRNA

The presence of ENAC mRNA in taste bud related tissues as well as other organs was examined utilizing reverse transcription-polymerase chain reaction (RT-PCR) using primers corresponding to the published ENAC nucleotide sequence (Canessa et al., 1993, Nature, 361:467–470).

PCR and Cloning

Ten µg total RNA from various tissues were reverse transcribed using 1 µg of oligo dT as primer in a 50 µl reaction which contained 500 µM deoxynucleotide triphosphates (dNTPs), 50 units of RNAse (Boehringer Mannheim), 200 units of Maloney murine leukemia virus-reverse transcriptase (MMLV-RT) (BRL) and a buffer of 50 mM Tris (pH 8.3), 50 mM KCl, 8 mM $MgCl_2$, and 10 mM dithiothreitol (DTT). One µl of the reverse transcription mix was used in a 25 µl PCR reaction containing 1.5 mM $MgCl_2$, 400 nM primers, 200 µM dNTP and 0.5 unit of Taq Polymerase (Boehringer Mannheim). PCR was conducted under high stringency conditions (35 cycles of 1 minute at 95° C., 2 minutes at 45° C. and 1 minute at 72° C.). The PCR product was visualized on a 1.5% agarose gel and the band corresponding to the expected size was subcloned and sequenced.

The cDNA clone generated by PCR was labeled using a random primer kit and [$^{32}$P]dCTP, and was used to screen a rat circumvallate papillae cDNA library under high stringency (50% formamide, 5×SSC 42° C. for hybridization and 1×SSC 55° C. for a final wash). Positive clones were purified and cDNA was prepared for restriction mapping and sequence analysis.

Figure 1:
FIG. 1 shows RT-PCR analysis of αENAC expression in various tissues.

FIG. 1 shows RT-PCR analysis of αENAC expression in various tissues. Ethidium bromide stained RT-PCR reaction product from rat olfactory epithelial tissue (Olf, lane 1), brain (lane 2), tongue epithelium adjacent to circumvallate papillae (TE, lane 3), circumvallate papillae (CV, lane 4), testis (Tes, lane 5); distal colon (colon, lane 6), kidney (Kid, lane 7), lung (lane 8), skin (lane 9) and the negative control with heavy water ($dH_2O$, lane 10). A 1 kb DNA ladder was used as a marker. The arrow indicates the expected size (609 bp) of PCR products using primers Ena-S2 (TTATGGATGATGGTGGCTTC) (Seq. ID NO: 1) as the forward primer and Ena-A2 (AGCACGGACGA-GCCAAACCA) (Seq. ID NO: 2) as the reverse primer. These primers correspond to the published ENAC nucleotide acid sequence 1162–1181 and 1752–1771, respectively. The presence of prominent bands was observed in kidney and colon. No mRNA was observed in the brain or testis. The most prominent band was observed in the lung, with an intensity several times greater than that of colon and kidney.

It was discovered that bands of comparable intensity occur in epithelial tissue of the circumvallate papillae and in epithelium tissue of adjacent tongue sections that lack circumvallate papillae. Olfactory epithelium displays a PCR band of similar intensity to bands in the tongue, while skin has a faint band. The PCR product from circumvallate papillae was subcloned and sequenced. A sequence which is identical to that previously reported (Canessa et al., 1993, Nature, 361:467–470) was observed.

Since PCR is not fully quantitative, the distribution of αENAC by Northern blot analysis was evaluated with a cDNA clone of αENAC obtained by high stringency screening of the circumvallate papillae cDNA library. Total RNA (30 µg) or poly($A^+$) RNA (5 µg) was prepared from various rat tissues or cultured cell lines (normal rat kidney epithelial-like cell line NRK-52E; human embryonic intestine cell line I-407 and human colon adenocarcinoma cell WIDR; obtained from the American Type Culture Collection), fractionated on 1% agarose/formaldehyde gels and blotted onto a nitrocellulose membrane. The entire insert (2.1 kb) of the cDNA clone isolated from rat circumvallate papillae cDNA library was released from plasmids and purified on an agarose gel. [$^{32}$P]labeled probes were prepared using the random oligonucleotide primer labeling kit (Boehringer Mannheim). The blot was hybridized in 50% formamide, 5×SSC hybridization buffer at 42° C. and washed with 0.1×SSC at 65° C. The blot was then exposed to X-ray film for 5 days at −70° C.

Figure 2:
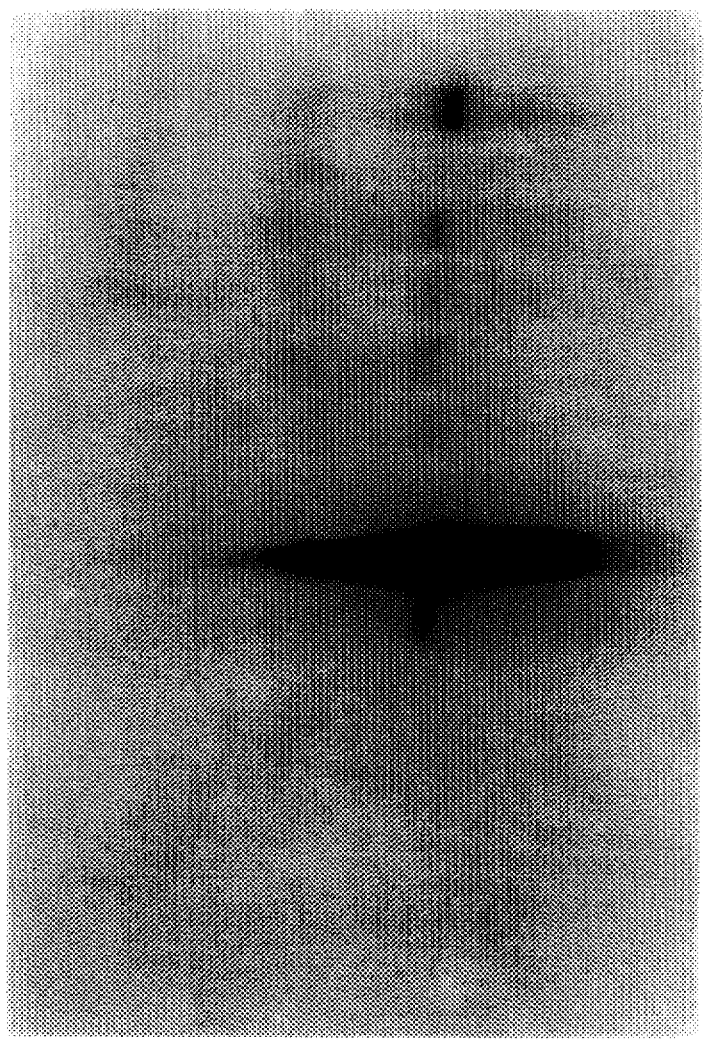
FIG. 2 shows Northern blot analysis of αENAC expression in various rat tissues and cell lines.

FIG. 2 shows Northern blot analysis of αENAC expression in various rat tissues and cell lines. A blot prepared from total RNA (30 µg) of rat brain (lane 1), poly (A)+mRNA (5 µg) of rat tongue tissue adjacent to circumvallate papillae (To poly (A), lane 2), total RNA (30 µg) from rat skin (lane 3), anterior tongue epithelium (TE, lane 4), olfactory epithelial tissue (Olf, lane 5), circumvallate papillae (CV, lane 6), tongue tissue adjacent to circumvallate papillae (To, lane 7), whole eye (lane 8), lung (lane 9), kidney (Kid, lane 10), testis (Tes, lane 11), skeletal muscle (Mus, lane 12), spleen (Sp, lane 13), rat normal kidney epithelia-like cell line (NRK) (lane 14), human embryonic intestine cell line (I-407) (lane 15), and human colon adenocarcinoma cell line (WDRK) (lane 16). The positions of 28s and 18s ribosomal RNA are indicated. From this library, a 2.1 kb partial-length cDNA clone was obtained and used for Northern blot analysis. Sequence analysis reveals that this partial clone is identical in sequence to the previously reported αENAC (Canessa et al., 1993, Nature, 361:467–470; Lingueglia et al., 1993, FEBS Lett, 318:95–99).

Northern blot analysis confirmed the results of PCR. The most prominent band was obtained in the lung. Bands in all tissues are about 3.5 kb, resembling previous reports (Canessa et al., 1993, Nature, 361:467–470). Substantial mRNA levels are evident in the kidney, while negligible levels occur in skin and in whole eye. Modest amounts are evident in olfactory epithelium. Interestingly, a continuous culture of rat kidney epithelium-like cells does not display αENAC mRNA, despite the high levels in kidney from intact rat. Similarly, no mRNA is observed in cell lines from human intestine or human colon cancer, rat spleen, rat muscle or rat testes.

In the tongue substantial amounts of mRNA occur in epithelium containing circumvallate papillae as well as adjacent tissue lacking circumvallate papillae. A strip of epithelium from the anterior region of the tongue was also found to contain substantial αENAC mRNA. A poly($A^+$) preparation of epithelium from an area of tongue adjacent to the circumvallate papillae lacking taste cells, displayed higher levels of mRNA, presumed to be due to the poly($A^+$) enrichment.

In situ hybridization utilizing a [$^{32}$P] cRNA probe generated from PCR products (450 bp) using primers Ena-S1 and Ena-A1 under moderate stringency hybridization was performed on rat tongue tissue sections. The PCR clone in a Bluescript vector containing a 450 bp insert (between primers Ena-S 1 and Ena-A 1) was used to generate antisense RNA probes with [$^{33}$P]UTP labeling. Sense RNA probes provided negative controls.

Three antisense oligonucleotides (45 mer) based on the published ENAC sequence (Canessa et al., 1993, Nature, 361:467–470) were also labeled with [$^{33}$P]dATP by the terminal transferase reaction for in situ hybridization on rat lung and colon sections. The sequences of these oligonucleotides are Ena-A7 (AAGTCATTCTGCTCTGT-GCGCAGTGTCAGGGACAAACCATTGTTG)(Seq. ID NO: 11), which correspond to the published nucleic acid sequence 1053–1098, ENA-A9 (CAGTTTATAATAGCAA-TAGCCCCAGGAGCTCTGCTTTCGGTAGTC)(Seq. ID NO: 12), which corresponds to the published nucleic acid sequence 1416–1461, and Ena-A6 (GCTGGGGAAGAT-GTGCTGAAGTGAGATATCCTCAGTTTTACAAGG)(Seq. ID NO: 13), which corresponds to the published nucleic acid sequence 2134–2179. Labeled probes were separated from unincorporated nucleotides by fractionation on a Sephadex G50 column.

Tissue sections (16 μm) were fixed in 4% paraformaldehyde, rinsed in phosphate buffered saline and digested with 10 μg/ml proteinase K at 37° C. for 30 min. Sections were then rinsed in 0.1M triethanolamine, acetylated in 0.25% acetic anhydride for 10 min, and dehydrated in a graded series of ethanol solutions. Hybridization was performed with $10^6$ cpm/100 μl of probe in 50% formamide, 10% dextran sulphate, 0.3M $MgCl_2$, 10 mM Tris pH=8, 1×Denhardt's solution, 0.5 mg/ml tRNA and 10 mM DTT overnight at 37° C. for oligonucleotide probes and at 55° C. for cRNA probes, respectively. Excess cRNA probe was removed by digestion with RNAse A (20 μg/ml) for 30 min and washed at a final stringency of 0.1×SSC at 60° C. for 30 min while excess oligonucleotide probe was removed by a final washing of 2×SSC at 55° C. for 1 hr. Slides were hand-dipped in Kodak NTB2 emulsion, exposed for 1–4 weeks at 4° C., developed and stained with Giemsa stain (Sigma). Photography was done with a Nikon Microphoto FX microscope.

Tongue areas enriched in taste buds, such as circumvallate and foliate papillae, were compared with the anterior dorsal and ventral epithelia which lack taste buds.

FIGS 3A-1 through 3A-4 and 3B-1 through 3B-6 show localization of ENAC mRNA in rat tongue epithelium. Panels 3A-1, 3A-2, 3B-1, 3B-3 and 3B-5 (×10) show brightfield views of cross-sections of a rat circumvallate papillae (3A-1), foliate papillae (3A-2), anterior dorsal region (3B-1, 3B-5) and anterior ventral region (3B-3) of tongue epithelium, hybridized with a [$^{33}$P] cRNA probe. Panels 3A-3, 3A-4, 3B2, and 3B4 show darkfield images of sections corresponding to the brightfield view. Panels 3B-5 and 3B-6 are brightfield and darkfield images of the rat anterior dorsal tongue epithelium hybridized with a sense cRNA probe. The taste buds are indicated by arrows.

In all of these regions except ventral epithelium, high densities of silver grains associated with the epithelium with negligible densities in the underlying muscle or glandular tissue were observed. In circumvallate and foliate papillae grain density is the same in taste and non-taste epithelium. Grain density appears similar in epithelium from areas with or without taste cells. Experiments utilizing a sense probe reveal no hybridization.

Extremely high densities of ENAC grains was found to occur in lung tissue localized to the epithelial layer of small bronchi and alveoli. FIGS. 4A-1 through 4A-4 and 4B-1 through 4B-4 show in situ hybridization of ENAC mRNA in peripheral tissues. Three oligonucleotides (45 mer) labeled with [$^{33}$P] were hybridized to adult rat lung (4A-1 through 4A-4) (×20) and distal colon (E–H) (×40) in light (4A-1, 4A-2, 4B-1, and 4B-2) and dark field (4A-3, 4A-4, 4B-3 and 4B-4) microscopy. High densities of autoradiographic grains are over regions of the lung containing alveoli (arrows), alveolar epithelium and the epithelium of small bronchi in (4A-1) and epithelial cells of colon (arrows) in (4B-1). An absence of grain accumulation in the epithelial and smooth muscle lanes of the blood vessel in (4A-1) and in lamina propria in (4B-1) (double arrows) was seen. Panels 4A-4 and 4B-4 are views of cross-sections of rat lung and colon hybridized with sense probe. Low levels of silver grains are distributed evenly over the epithelial layer and smooth muscle of blood vessels. High densities of ENAC grains occur in the epithelium of the distal colon, but not in the lamina propria. Sense probes reveal a low background of grains in both lung and colon.

Besides native αENAC, two alternatively spliced transcripts, αENACa and αENACb, have now been identified. The sole form of αENAC cloned from epithelial tissues of mammalian species displays substantial homology to mechanosensitive proteins associated with degeneration of neurons that mediate touch sensitivity in *Caenorhabditis elegans* (Lingueglia et al., 1993, *FEBS Lett*, 318:95–99). To identify homologues of αENAC, two degenerate oligonucleotides that correspond to sequences conserved between rat αENAC and *C. elegans* protein mec-4 and deg-1 (Canessa et al., 1993, *Nature*, 361:467–470) were used as primers for RT-PCR. The degenerate primers were designed based on the published αENAC sequence. Sense primer αEN-S3 (CAGGT(G/C)GAATTC(A/G)(C/T)TC(A/C/T) TG(C/T)T(T/C)CA)(Seq. ID NO: 4) is the forward primer that corresponds to the αENAC amino acid sequence CIHSCFQ(443–449). Antisense primer αEN-A3 (GATCCACTCGAGNGA(T/C)TTNACNGANGGCCA) (Seq. ID NO: 7) is the reverse primer that corresponds to αENAC amino acid sequence WPSVKS (520–525).

These primers give rise to several PCR products (246, 223 and 167 bases). Deletion of 23 nucleotides and 79 nucleotides in two of the PCR products introduces premature stop codons and results in the production of functional αENAC proteins shortened by 200 and 217 amino acids (αENACa and αENACb, respectively) at the carboxyl terminus compared to native αENAC protein.

As shown diagrammatically in FIG. 5A, degenerate sense (αEN-S3) and antisense (αEN-A3) oligonucleotides were used to amplify cDNA made from rat circumvallate papillae tissue containing taste cells. The indicated PCR products which encode a portion of protein between two putative transmembrane (TM) domains (black box) were obtained. In FIG. 5A, "wt" refers to native αENAC; "a" refers to alternatively spliced form αENACa and "b" refers to alternatively spliced form αENACb. Sequence analysis of the PCR products (αENAC, αENACa and αENACb) shows that 23 bases and 79 bases, as indicated in FIG. 5B by space between the black boxes, have been deleted in αENACa and αENACb, respectively, with insertion of a premature stop codon.

PCR product, αENACa shows a deletion of 23 bases. The rest of the sequence was identical to αENAC. The deletion occurs between bases TCCTGGG (Seq. ID NO: 3) and GGCGCCT (Seq. ID NO: 14) and is associated with a reading frame shift that results in a sequence change of 17 amino acids followed by a stop codon.

PCR product αENACb shows a 79 base deletion that starts with the same splicing site (TCCTGGG) (Seq. ID NO: 3) as αENACa, and a premature stop codon immediately follows the splicing site. Thus, both alternatively spliced transcripts share the same splicing cite CTCCTGGG (Seq ID NO: 3). FIG. 5B shows the nucleotide and amino acid sequence comparisons of published native αENAC and alternatively spliced forms αENACa and αENACb. These premature stop codons will generate a deletion of 200 or 217 amino acids at the carboxyl terminus in the native αENAC that may result in a shorter protein with 498or 481 amino acids, compared to the expected native αENAC protein (698 amino acid).

To ascertain whether the splicing variant αENACa possesses the same sequence as native αENAC except for the 23 base deletion, PCR analysis utilizing primers selective for αENACa and primers selective for native αENAC was performed. Specific primers for native and alternatively spliced αENACa were used to amplify cDNAs prepared from different tissues. The antisense primers αEN-A1 (TTATAATAGCAATAGCCCCA) (Seq. ID NO: 12) for αENAC and αENa-A1 (TCCAAGGAGAAGGCGCCCCCA) (Seq. ID NO: 5) for αENACa, respectively, were used with the oligonucleotide (S1) encoding the N-terminal sequence (GAGGGCAGCCTGGATGCGG) to amplify cDNA encoding the N-terminal region of protein. The sense primers αEN-S2 (CAGAGCTCCTGGGGCTATTG) for αENAC and αENa-S2 (CAGAGCTCCTGGGGGCGCCTT) for αENACa, respectively, were used with antisense oligonucleotides (A2) encoding the C-terminal sequence (CTTGAATTCTCTCAGAGCGCC) to amplify products encoding the C-terminal portion of this channel. The specificity of these primers was verified by RT-PCR with RNA prepared from HEK-293 cells transfected with either αENAC or αENACa cDNA.

RNA was prepared from a human embryonic kidney cell line (HEK-293) transfected with native αENAC or the alternatively spliced form αENACa to serve as templates for RT-PCR analysis of the specificity of the oligonucleotide primers. PCR was conducted under the same conditions as above described except that the annealing temperature was 65° C. The PCR products were separated in 1% agarose gel, transferred onto nitrocellulose membranes and hybridized with the entire cDNA fragment (3 kb) of αENAC that was labeled with $^{32}$P. The PCR Southern blot was conducted under high stringency (50% formamide, 5XSSC 42° C. for hybridization and 1XSSC 65° C. for a final wash) and exposed to x-ray film. Genomic DNA Southern blot analysis indicated that a single gene accounts for the alternatively spliced variants (αENACa and αENACb) and the native form of αENAC. Using a sense or antisense primer specific for the native form of αENAC along with a primer selective for the C-terminal or N-terminal portion of αENAC, a signal was detected in the cells transfected with the native form but was not detected in cells transfected with αENACa. By contrast, utilizing primers selective for αENACa, a signal was detected in cells transfected with αENACa, but not in those transfected with the native channel.

Figures 6A, 6B:
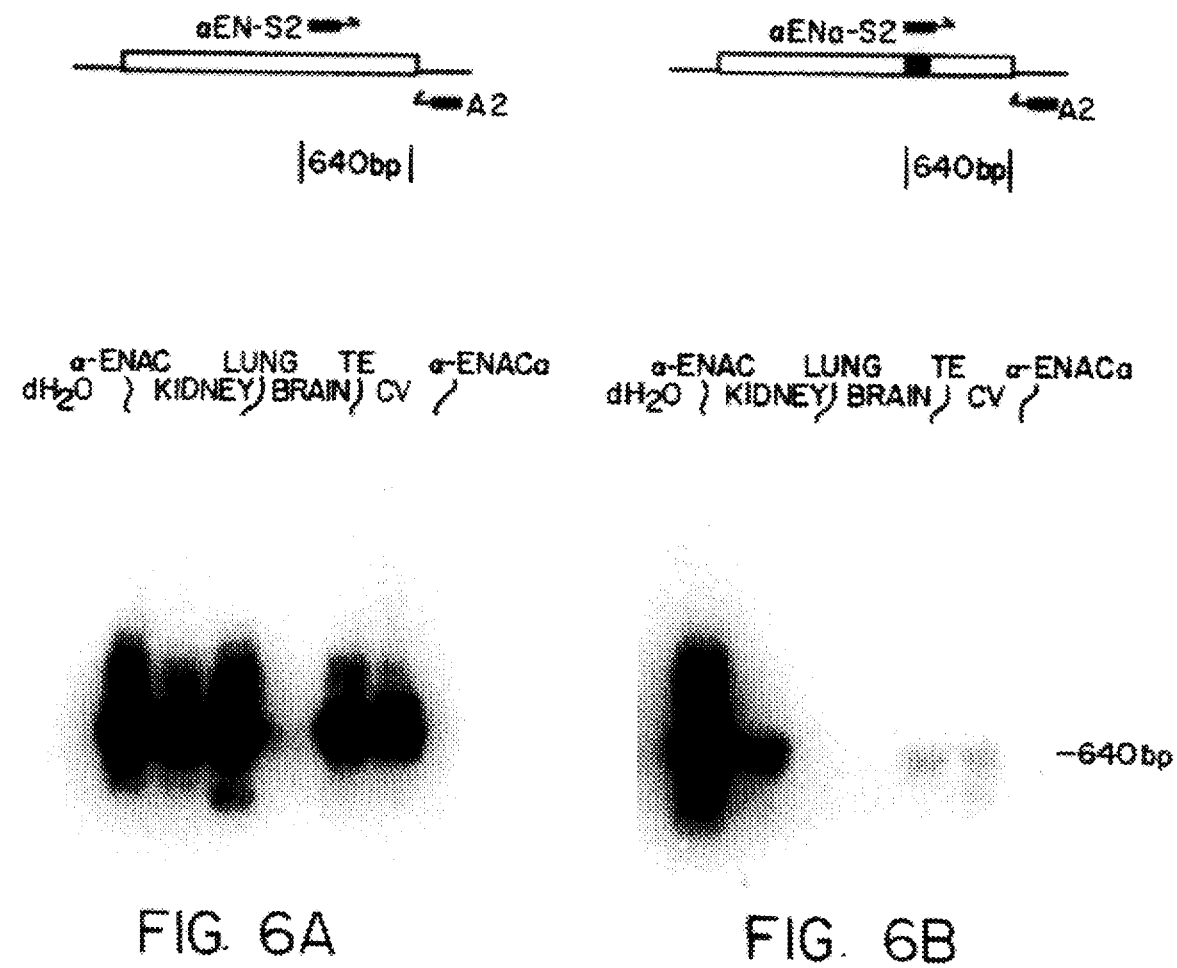

FIGS. 6A and 6B show amplification with specific sense primers and C-terminal primers. FIGS. 6C and 6D show amplification with specific antisense primers and N-terminal primers. In FIGS. 6A–D, dH$_2$O is water without cDNA template; αENAC and αENACa represent HEK-293 cells transfected with native αENAC cDNA and alternatively spliced αNACa cDNA, respectively; TE represents rat tongue epithelia and CV represents tongue taste tissue enriched in circumvallate papillae. The sizes of expected PCR products are also indicated in these Figures. PCR products from different tissues utilizing primers for αENACa display the same size as those obtained with primers for native αENAC. Restriction enzyme digestion and partial cDNA sequence analyses of these PCR products indicate that, except for the deletion, the two forms of αENAC possess the same sequence.

As disclosed above, native αENAC is highly expressed in lung, kidney and tongue but not in brain. Utilizing primers for the C-terminal portion of the channel, similar relative levels of native αENAC in taste bud enriched tissue as in epithelium obtained from the entire tongue have been confirmed (FIGS. 6A and 6B). PCR signals for αENACa are substantially lower than for the native form. In contrast to the native form, αENACa expression is undetectable in the lung, though substantial signals are evident in kidney and tongue. As with the native form, αENACa is not detected in the brain. PCR analysis utilizing a primer selective for the N-terminal portion of αENAC along with an antisense primer from the mid region of the channel selective either for the native channel or αENACa was also conducted (FIGS. 6C and 6D). The results from kidney and lung confirm the findings obtained with the primers directed toward the C-terminal region. Thus, analysis of the N-terminal portion of the protein, with primers selective for the native channel, reveals comparable expression in the lung and kidney, whereas the αENACa selective primer expression is less in the kidney and undetectable in the lung.

Figure 7A:
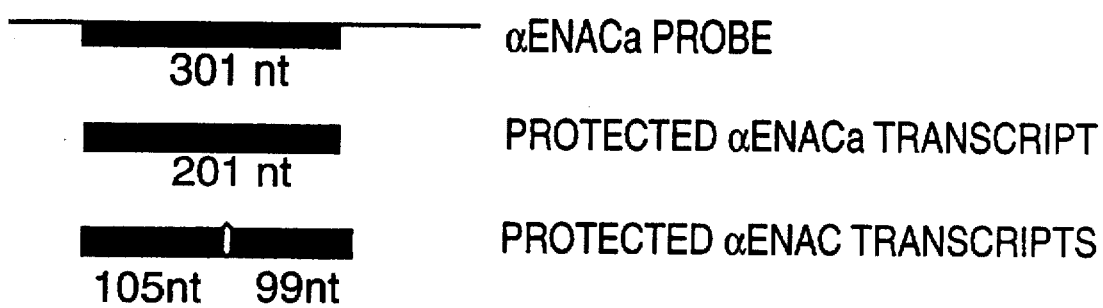
FIG. 7A shows RNAse protection analysis of an alternatively spliced ENAC in various rat tissues.
Figure 7B:
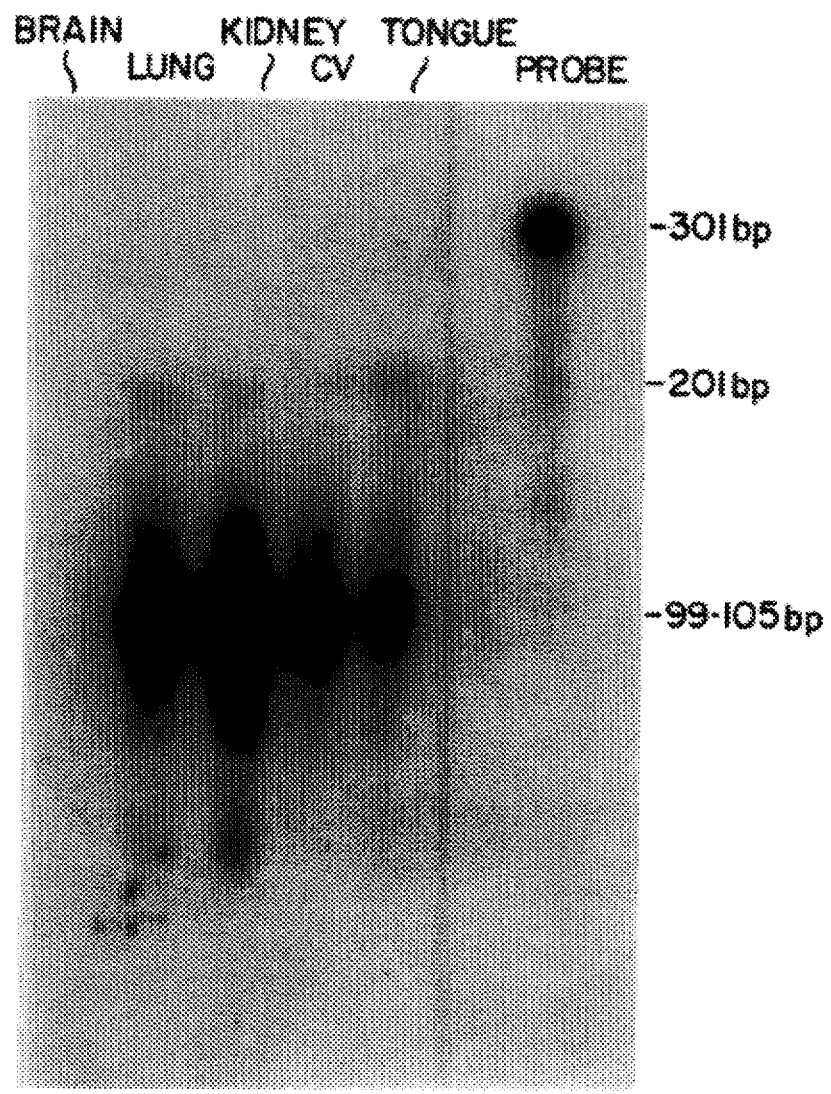
FIG. 7B shows genomic Southern Blot analysis of rat αENAC gene.
Figure 9A:
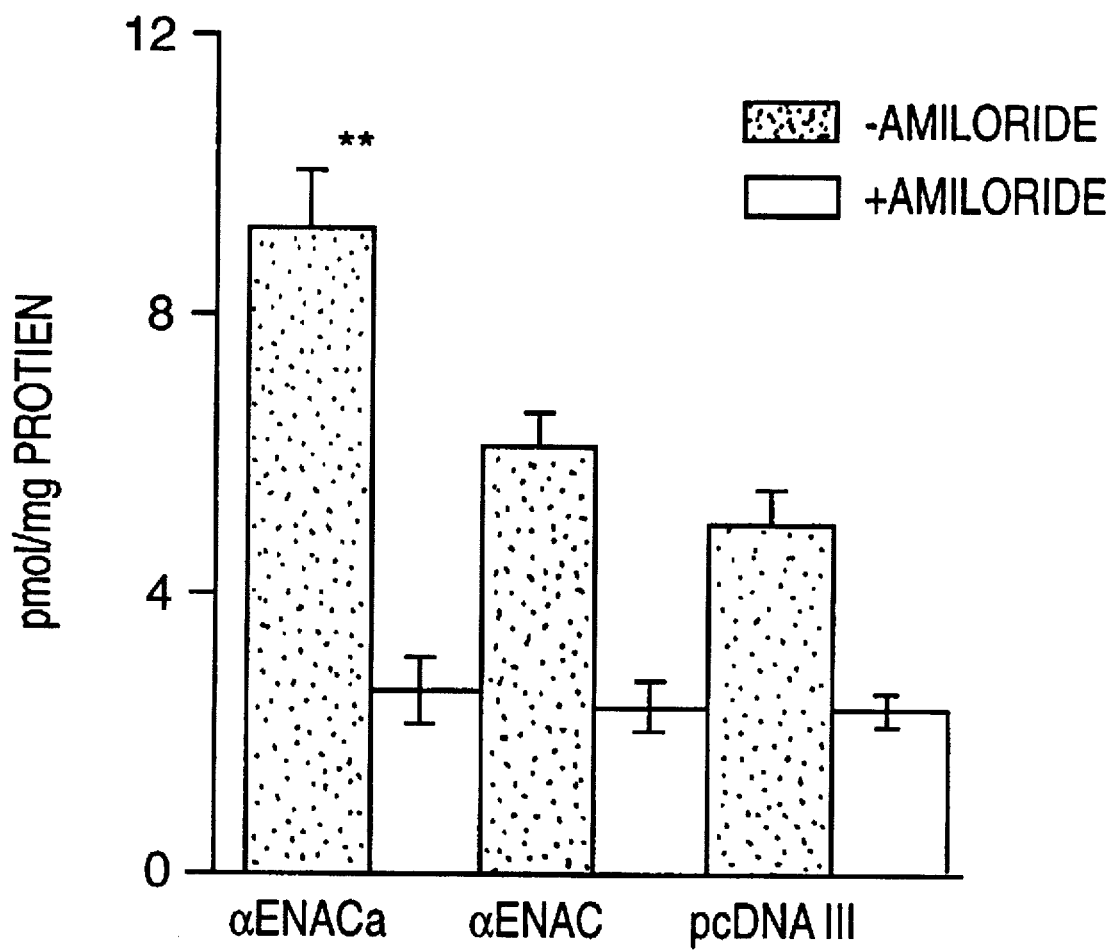
FIG. 9A shows comparison of binding of [$^3$H]phenamil to membranes from HEK-293 cells transfected with αENACa, αENAC or control (non-transfected HEK-293 cells).
Figures 1, 9B:
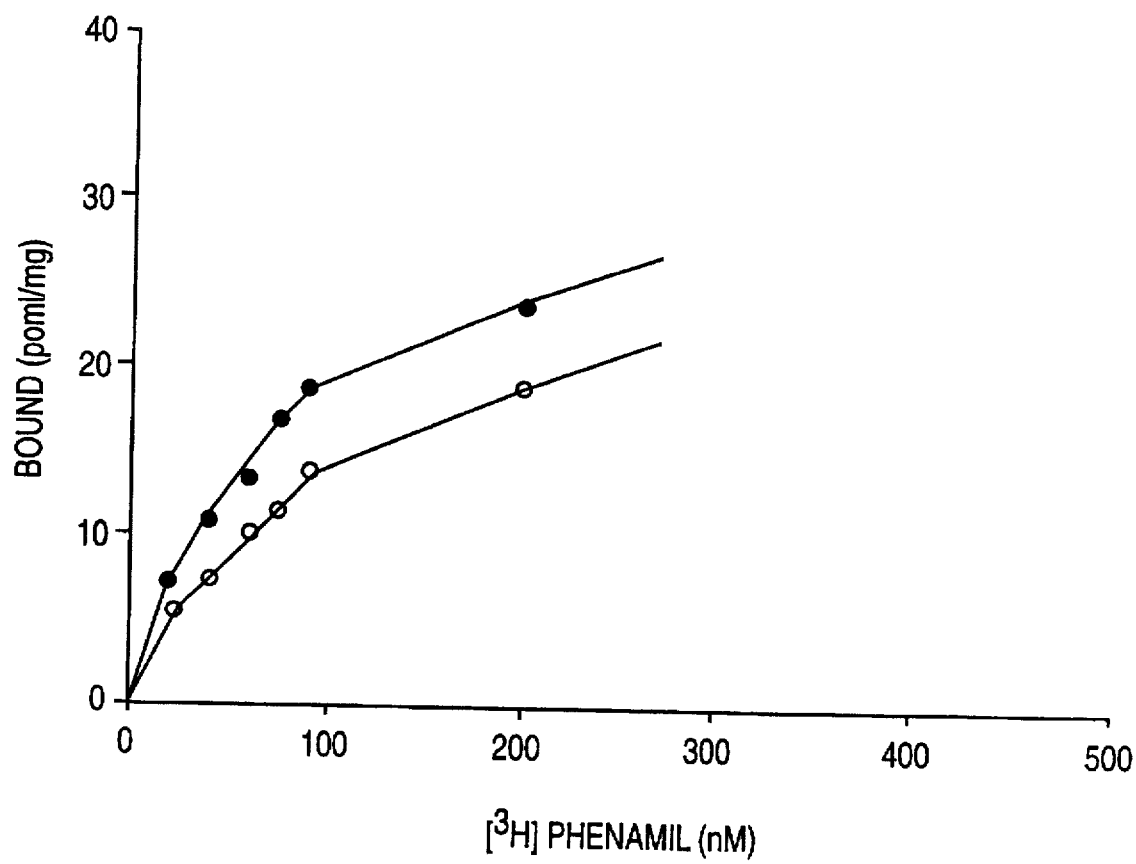
Figures 2, 9B:
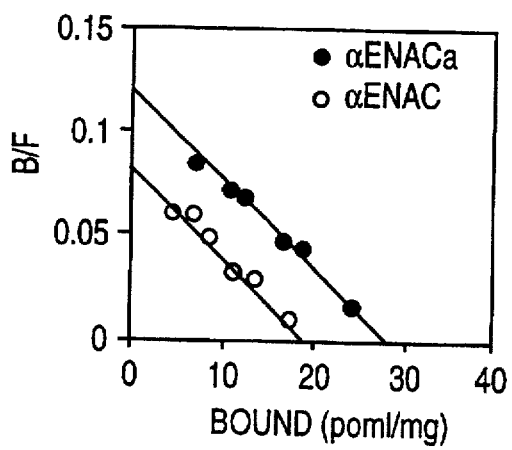

Since quantifying relative amounts of RNA is difficult with PCR technology, protection analysis using an RNA probe derived from a PCR clone for αENACa was conducted in order to verify the tissue distribution of αENACa and the native channel (FIG. 9). In the RNase protection assay, the alternatively spliced cDNA clone αENACa identified by PCR using primers αEN-S3 and αEN-A3 was used to generate a [$^{32}$P]UTP antisense RNA probe using T3 RNA polymerase. Twenty μg total RNA from various tissues were hybridized with the antisense RNA probe (1×10$^5$ cpm) in 20 μl reaction buffer (80% formamide, 40 mM PIPES (pH 6.4), 400 mM NaOAc (pH 6.4), 1 mM EDTA) at 55° C. for 18 hours. Total RNA from rat brain, lung, kidney, tongue circumvallate papillae (CV) and tongue epithelial tissue adjacent to circumvallate papillae (TE) were hybridized with the [$^{32}$P]antisense RNA probe (310 nt) transcribed from a Bluescript plasmid containing alternatively spliced cDNA αENACa fragment (201 nt, black box). RNase A and RNase T1 (1:100 dilution) were employed to digest unprotected RNA, following the instructions of the RNase protection assay kit (Ambion). The protected pieces of RNA were fractionated on a 5% acrylamide gel and visualized by exposure to Kodak X-ray film for 4 days. The protected size (201 nt) of transcript for αENACa as well as the expected size of transcripts for αENAC (99 and 105 nt) digested by RNase are indicated in FIG. 7. The additional protected size suggests the existence of other alternatively spliced forms. As observed in PCR analysis, levels of native αENACa transcripts that have been digested by RNase to 99–105 nucleotides (nt) are substantially higher than those of αENACa (201 nt). The highest densities of native αENAC transcripts are observed in lung and kidney, with levels in kidney being somewhat higher than those in lung. Substantial and similar levels occur in epithelial tissue of the tongue and in taste bud enriched tissue. No expression of αENAC is observed in brain. RNase protection reveals a protected size of 201 nt for αENACa transcripts. αENACa levels in epithelial tissue of the tongue are slightly higher than in taste bud enriched regions.

As in PCR experiments, RNase analysis reveals no expression of αENACa in the brain. αENACa levels are comparable in lung and in kidney, in contrast to PCR analysis which reveals no expression in lung. RNase assay also reveals additional sizes of protected transcripts, implying that other alternatively splicing occurs in this region, as observed for αENACb. Thus, RT-PCR and RNase protection assays demonstrate that αENACa is expressed to a lesser extent than native αENAC in kidney, lung and taste tissue.

Figure 8:
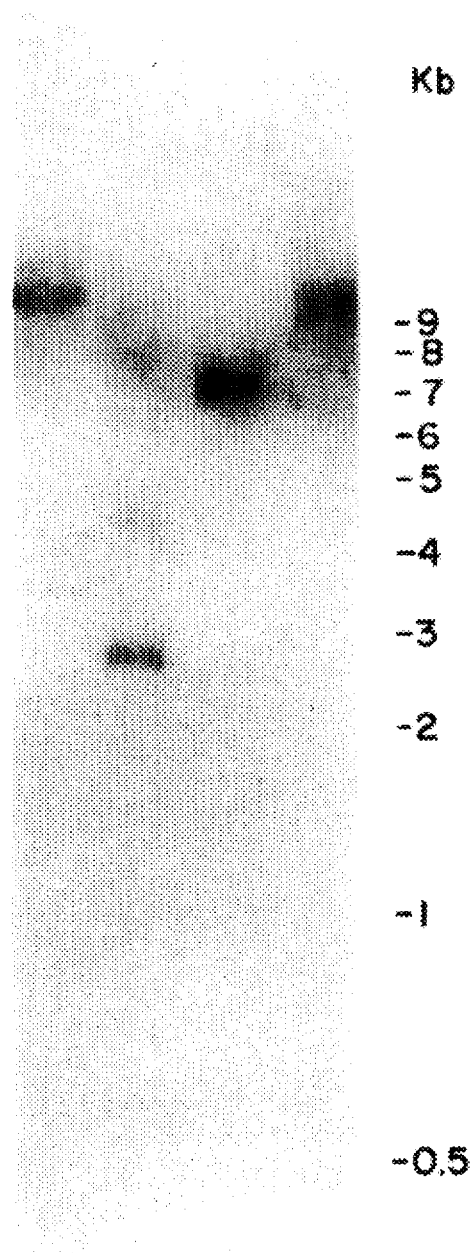
FIG. 8 shows genomic Southern Blot analysis of rat αENAC gene.

To ascertain whether alternatively spliced transcripts for αENAC derive from a single gene or from multiple genes, genomic Southern blot analysis was conducted (FIG. 8). A probe comprising a 223 base PCR product obtained from αENACa was employed. Genomic DNA was prepared from rat testis following standard procedures. Restriction enzyme digestion was conducted with EcoR I, Hind III, BamH I and Xba I. Five μg rat testis genomic DNA digested by the enzymes EcoR I, Hind III, Bam I and Xba I were fractionated in 0.7% agarose gel and hybridized to a [$^{32}$P] cDNA probe generated from alteratively spliced PCR products αENACa (223 bp). Hybridization and washing were carried out under moderate stringency: 6XSSC at 55° C. and wash 2XSSC at 50° C. The blot was exposed to the X-ray film for 4 days. In all instances, a single strong hybridization band was observed. Since αENACa differs from native αENAC only in a 23 base deletion, it should hybridize to genes for native and alternatively spliced forms of the channel. Accordingly, the existence of one band indicates that a single gene accounts for native and alternatively spliced forms of αENAC.

Amiloride sensitive sodium channels have been extensively characterized in intact tissues by the binding of radioactive ligands. Of those employed, [$^3$H]phenamil, an amiloride analog, possesses the highest affinity for the channel and has provided the most abundant and selective binding. Utilizing stably expressed αENACa in HEK-293 cells, association of αENACa with ligand binding selective for amiloride was demonstrated. To limit variations in expression of individual clones, a pool of stably expressed cells (about 30 clones) that were mixed and propagated 3–4 times were used for the binding assay.

The full length cDNA of αENAC obtained by screening a rat taste cDNA library as described above (also described by Li et al., 1994, Proc. Natl. Acad. Sci. USA, 91:1814–1818, the disclosure of which is incorporated herein by reference) was cut with Not I and Xho I and inserted into an expression vector pcDNA-III (Invitrogen). The PCR product of the alternatively spliced form αENACa was cut with Bcl I to replace the corresponding region of native αENAC in pcDNA III. Thus the native form (αENAC) and an alternatively spliced form (αENACa) of the alpha subunit of ENAC in the expression vector was constructed for stable expression in HEK-293 cells. DNA (10 μg) was then transfected into HEK-293 cells by the calcium phosphate technique. Stable expression clones of cells were selected by exposure for 4–6 weeks to a medium containing 500 μg/ml G418.

Transfected HEK-293 cells were harvested in cold (4° C.) binding buffer containing 1 mM EDTA, 15 mM Tris-HCl (pH 7.7), 1 μM pepstain A, 0.1 μM aprotinin, 0.1 mM phenylmethylsulfonyl fluoride and 10 μM leupeptin. Cells were then homogenized, centrifuged and the pellet resuspended in the binding buffer at 1–2 mg/ml concentration. The reaction mixture (0.2 ml) containing [$^3$H]phenamil (2.8 C/mmol) and 100 μg protein was incubated at 4° C. for 90 minutes and the reaction terminated by rapid filtration through Whatman GF/B glass fiber filters pretreated with 0.3% polyethyleneimine. Amiloride (Sigma) suspended in 50% dimethylformamide was used as a competitor in the binding assay. Proteins was assayed by a kit (Pierce) with bovine serum albumin as a standard.

[$^3$H]phenamil binding in HEK-293 cells transfected with native αENAC or alternatively spliced αENACa are compared in FIGS. 9A and 9B. Binding of [$^3$H]phenamil to membranes from HEK-293 cells transfected with αENACa, αENAC or expression vector pcDNA III alone were compared. Concentrations of [$^3$H]phenamil and amiloride were 50 nM and 1 mM, respectively. Values presented are means±standard error (n=4–5), statistically significant (p<0.05) difference from αENAC or pcDNA III. As can be seen in FIG. 9A, levels of [$^3$H]phenamil binding are not significantly greater in cells transfected with native αENAC than in HEK-293 cells transfected only with the expression vector. By contrast, [$^3$H]phenamil binding is significantly higher in cells transfected with native αENAC than in those transfected only with the expression vector or αENAC.

Saturation analysis involving a range of [$^3$H]phenamil concentrations, as shown in FIGS. 9B-1 and 9B-2, also establish, also establishes that [$^3$H]phenamil binding is higher in αENACa transfected cells ($B_{max}$=28 pmol/mg protein) than in those transfected with native αENAC ($B_{max}$=18 pmol/mg protein). In cells transfected with αENACa the apparent Kd is 260 nM and $B_{max}$ is 28 pmol/mg protein whereas in cells transfected with αENAC Kd is 270 nM and $B_{max}$ is 18 pmol/mg protein. Each point represents results from two experiments using different passages of transfected cells. The binding affinity in αENACa transfected cells (Kd=260 nM) is not significantly different from that in αENAC transfected cells (Kd=270 nM).

Figure 10:
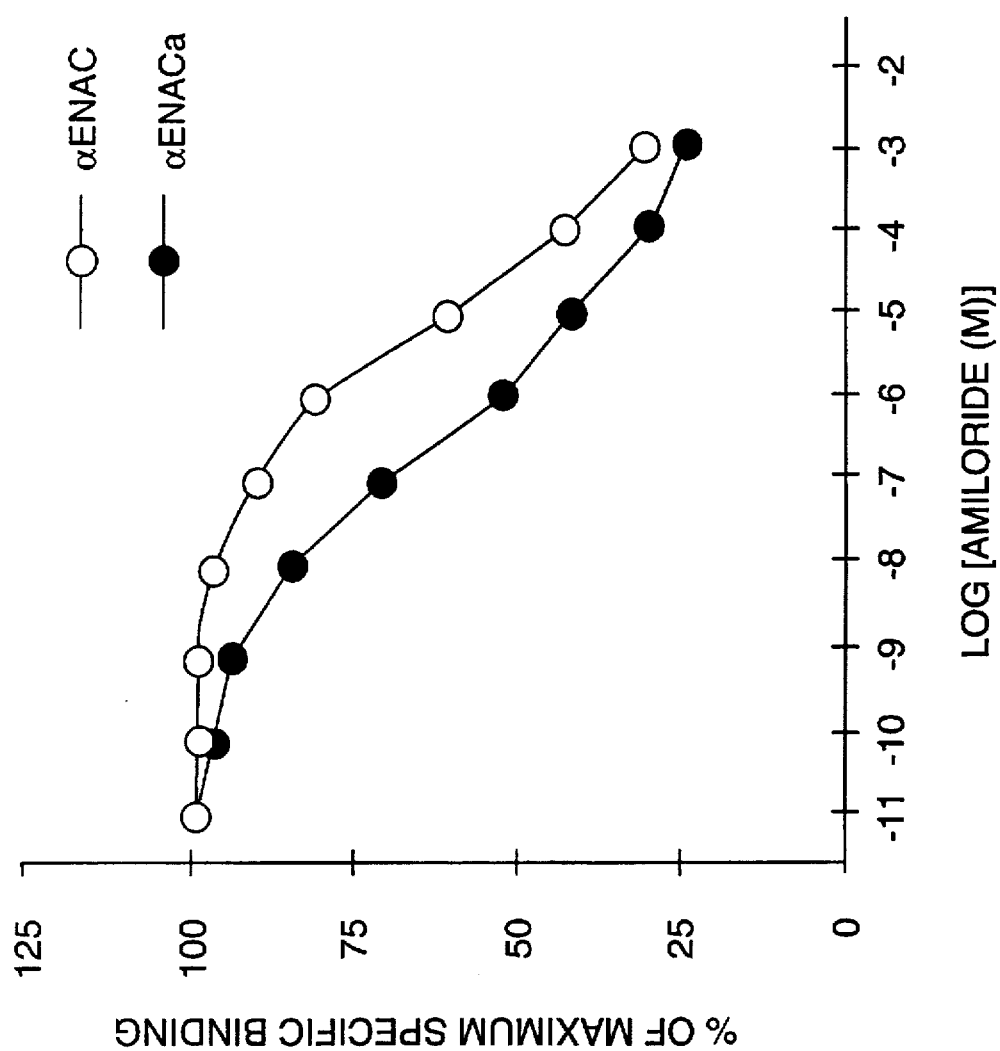
FIG. 10 shows inhibition of binding of [$^3$]phenamil to membranes from HEK-293 cells transfected with αENACa or αENAC by various concentrations of amiloride.

As shown in FIG. 10, binding of [$^3$H]phenamil to membranes from HEK-293 cells transfected with αENACa or αENAC was inhibited by various concentrations of amiloride. Membrane protein (100 μg) was incubated with 50 nM [$^3$H]phenamil in the absence or presence of increasing concentrations of amiloride. Three independent experiments were performed in duplicate. Results are presented of a typical experiment with values varying less than 20%. Amiloride is about 10 times more potent in competing for [$^3$H]phenamil binding in cells transfected with αENACa than in cells transfected with the native channel.

Transfection of αENACa into HEK-293 cells leads to a doubling of specific [$^3$H]phenamil binding whereas transfection of the native channel does not enhance binding. Recently, Canessa et al. (Nature, 1994, 467:463–467) have cloned two new ENAC subunits, designated β and γ. While the α subunit of ENAC confers sodium channel activity, these investigators report that such channel activity is increased by orders of magnitude in the presence of all three subunits. αENAC has previously been shown to be relatively unstable when expressed alone in Xenopus oocytes, presumably because of stacking in the endoplasmic reticulum (Lingueglia et al., 1994, J. Biol. Chem., 1993, 269:13736–13739). While not wishing to be bound to a particular theory, the shortened protein generated by αENACa may be more stable or readily translocated to the cell membrane in HEK-293 cells than the native channel generated by αENAC transfection. [$^3$H]phenamil binding in the untransfected HEK-293 cells may reflect endogenous amiloride-sensitive sodium channels. Conceivably αENACa transfection elicits [$^3$H]phenamil binding better than transfection of the native channel because the alternatively spliced channel can better associate with other subunits of this channel in HEK-293 cells. It may also be that αENAC of rat origin associates poorly with the β and γ subunits of HEK-293 cells, which are of human origin. It is also conceivable that the [$^3$H]phenamil binding in the untransfected HEK-293 cells is not attributable to amiloride-sensitive sodium channels. Lazdunski et al. (Novotny et al., 1994, J. Biol. Chem., 269:9921–9925) recently showed that the enzyme diamine oxidase binds [$^3$H]phenamil with high affinity and a drug specificity similar to that observed with amiloride-sensitive sodium channels. Despite the difficulty in explaining differences between the behavior of transfected αENACa and the native channel, it is clear that αENACa confers specific [$^3$H]phenamil binding activity.

Identification of alternatively spliced forms of αENAC indicates heterogeneity of alpha subunits of amiloride-sensitive sodium channel that may account for the multiple species of proteins observed during purification of this channel (Benos et al., 1986, *J. Biol. Chem.*, 262:10613-10618). Multimeric associations of homologous subunits may explain varying binding affinities reported for amiloride in epithelial sodium channels (Barbry et al, 1989, *Biochemistry*, 28:3744-3749; Vigne et al., 1989, *J. Biol. Chem.*, 264:7663-7668; Oh et al., 1992, *J. Biol. Chem.*, 267:18498-18504). Differential dynamics of α and γ subunits in intact organisms have been recently observed. Thus, salt depletion enhances mRNA expression of the γ but not the α subunit even though salt depletion markedly augments levels of α subunit protein (Renard et al., 1994, *J. Biol. Chem.*, 269:12981-12988). These findings suggest that the α subunit protein is relatively labile and is stabilized by augmented expression of the γ subunit. Because of the critical importance of ways in which the subunits are combined, the alternatively spliced α subunits may influence substantially the channel activity of the multimeric protein. The experiments characterizing phenamil binding in transfected cells described herein also imply that the N-terminal portion of αENAC protein can confer amiloride binding.

Based on published electrophysiological data and the discovery that ENAC occurs in epithelial layers of non-taste, as well as taste cells, a model of salty taste transduction mediated has been constructed.

It appears that non-taste cells are of crucial importance for salty taste perception. It has been shown that transepithelial sodium currents are sensitive both to amiloride and ouabain. (Heck et al., 1984, *Science*, 223:403-405; DeSimone et al., 1981, *Science*, 214:1039-1041). Since the great majority of cells in these preparations are non-taste cells, ENAC in non-taste cells appear functional. By analogy with the localization of ENAC in other organs (Tousson et al., 1993, *J. Cell Sci.*, 349:362), ENAC in lingual epithelia are presumed to be located in the apical region of the cell. By contrast, the sodium-potassium transporters which pump sodium outside the cell, are located in the basolateral surface of the cells. Accordingly, the movement of sodium is from the apical to the basal surface of cells. Thus, exposure to levels of NaCl that stimulate salty taste will cause a substantial augmentation in the sodium concentration in the interstitial fluid at the basolateral surface of taste and non-taste cells.

Interestingly, although ENAC molecules are present in the dorsal epithelium of tongue, they are absent from the ventral epithelium. This is consistent with the finding that rat dorsal lingual epithelium, but not ventral epithelium, is permeable to NaCl (DeSimone et al., 1981, *Science*, 214:1039-1041). In taste cells the sodium current provides the depolarization which triggers firing of the sensory nerves. In non-taste cells the same sodium current provides elevated levels of sodium in the interstitial space that facilitate accumulation of chloride as a counter anion to sodium. The role of this transepithelial passage of chloride in taste is indicated by findings that chorda tympani responses to sodium gluconate and sodium acetate are much less than to sodium chloride (Ye et al., 1991, *Science*, 254:724-726). All cells in the lingual epithelium are coupled by tight junctions so that anion movement is restricted (Ye et al., 1991, *Science*, 254:724-726; Simon, 1992, *Mol. Cell Biochem.*, 114:43-48). A small anion such as chloride may diffuse to the interstitial fluid, while the passage of gluconate, acetate and other large anions is hindered. The requirement of chloride for salty taste transduction emphasizes the importance of anion passage for the transduction process. The chloride in the extracellular space presumably accentuates depolarization of the taste cells with the negative charge contrasting to the relatively positive cellular interior. This model in which ENAC in non-taste cells are critical to salty taste may also be relevant to other forms of taste.

Figure 11:
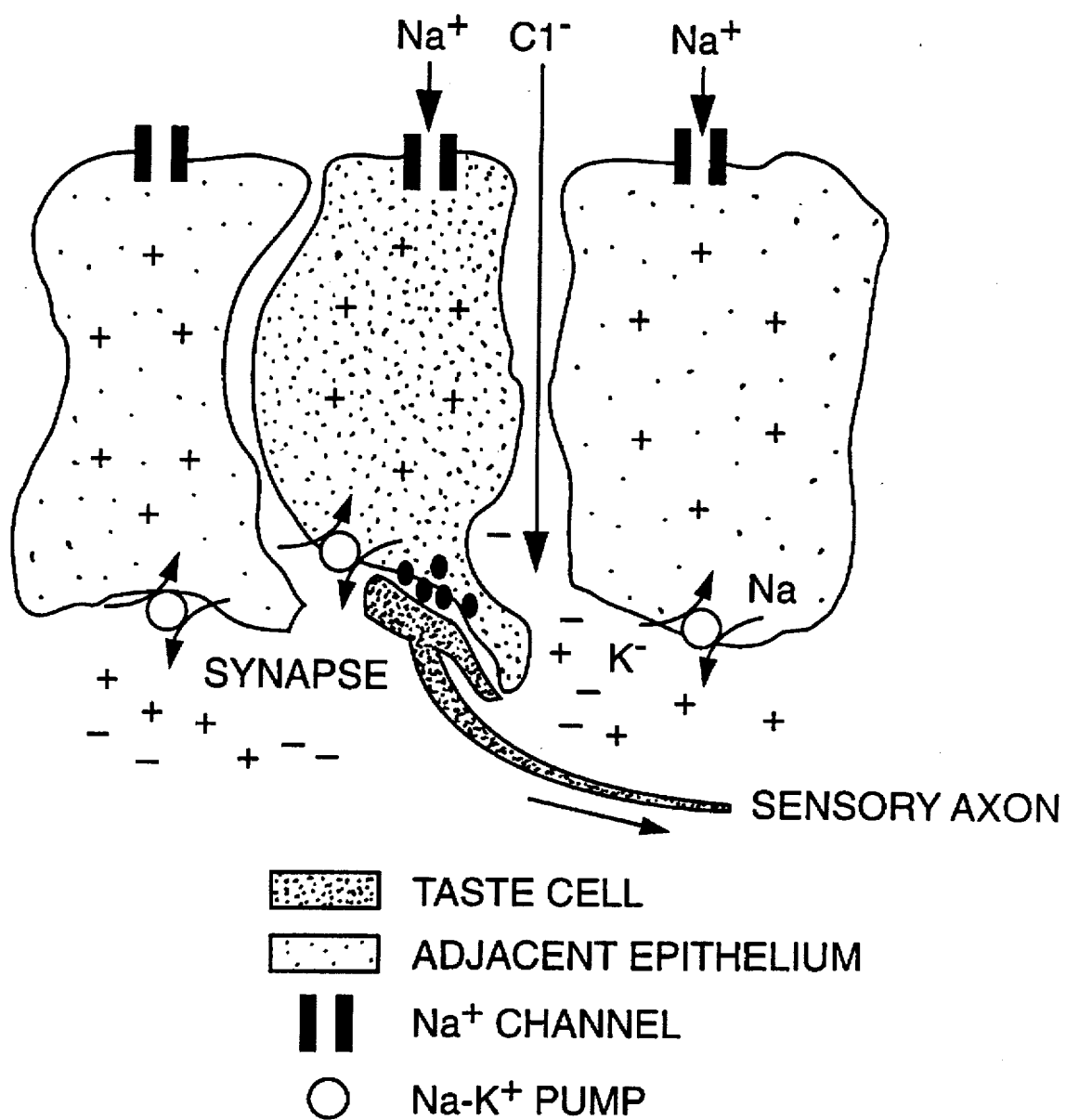
FIG. 11 suggests a model of salty taste transduction mediated by taste cells and adjacent epithelial cells.

FIG. 11 illustrates diagrammatically the proposed model for salty taste transduction mediated by ENAC in taste cells and in adjacent epithelial cells. Influx of sodium through apical membrane $Na^+$ channels of taste receptor cells depolarizes them and triggers the release of neurotransmitter to cause firing of the sensory axons. ENAC in adjacent non-taste cells are critical in maintaining the depolarized state of the taste cells. ENAC in the non-taste cells, along with the sodium-potassium transporter at the basolateral surface of these cells, causes a marked augmentation in the interstitial basolateral concentration of sodium when salty amounts of NaCl are applied to the tongue. This interstitial sodium promotes the passage of chloride through the tight junctions between cells to serve as a counter anion. The increased negative charges in the extracellular environment of the taste cell augment the depolarization of the taste cells. Evidence for this notion comes from electrophysiologic studies showing that signal transduction for salty levels of sodium is greatly diminished when chloride is replaced by gluconate or acetate, which are less able to penetrate the tight junctions between cells in the lingual epithelium. The non-taste cells are of particular importance, because they constitute the great majority of the cells in the lingual epithelium and so are the major determinants of the ionic composition of the fluid bathing the taste cells.

ENAC in non-taste cells are likely to play a major role in other taste modalities. In the case of sour taste, protons depolarize the taste cell and this depolarization is presumably enhanced by augmented negative charges in the extracellular fluid. Since all taste modalities involve depolarization of the taste cell, activation of ENAC in non-taste cells by the increased sodium content of saliva when tastants are applied would augment such depolarization. Thus, sour taste involves the passage of protons through ion channels. The proton current depolarizes taste cells to initiate signal transduction. Cells that respond to sour stimuli also respond to sodium, albeit to a lesser degree, while NaCl responsive cells are affected somewhat by sour tastants (Gilbertson et al., 1992, *J. Gen. Physiol.*, 100:803-824). Since sour taste in mammals is blocked by amiloride (Gilbertson et at., 1993, *Neuron*, 10:931-942; Gilbertson et al., 1992, *J. Gen. Physiol.*, 100:803-824), it is likely that some form of ENAC constitutes the sour taste receptor. If the principal form of ENAC cloned is the salty taste receptor, an alternatively spliced form of ENAC, such as the one herein identified, may represent the sour taste receptor.

ENAC in non-taste cells may regulate yet other forms of taste perception. Sweet taste is thought to involve G-protein coupled receptors linked to the stimulation of adenylyl cyclase (Striem et al., 1989, *Biochem. J.*, 260:121-126; Tonosaki et al., 1988, *Nature*, 331:354-356). Sweet taste perception is blocked by amiloride (Schiffman et al., 1983, *Proc. Natl. Acad. Sci. USA*, 80:6136-6140 and Mierson et al., 1988, *J. Gen. Physiol.*, 92:87-111). Sweet perception may be associated with ENAC activities in non-taste cells due to the stimulation of a flow of saliva by a tastant, which stimulated saliva contains sodium concentrations of about 60 mM, more than 10 times the basal sodium concentration of saliva (Dawes, 1969, *Arch. Oral. Biol.*, 14:277-294). This elevated sodium concentration should suffice to activate ENAC. The consequent increased interstitial chloride would accentuate the depolarization of the taste cells responding to sugar just as they enhance the response of taste cells responding to salt. In fact, application of low concentrations of salt to the tongue augments sweet taste responses (Kumazawa et at., 1990, *J. Gen. Physiol.*, 95:1007–1018). Since all taste transduction involves depolarization of taste cells, ENAC in non-taste cells may participate in signal transduction for all taste modalities, including umami taste, which is blocked by amiloride (Nakamara et at., 1991, *Brain Res.*, 541:21–28) and bitter taste.

The foregoing experiments have led to the localization of a cloned ENAC in epithelial layers of non-taste as well as taste cells. The localization of a cloned ENAC has led to the discovery of a method for identifying substances with a salty taste as well as agents that can block salty taste. Such a method enables the identification and development of salt substitutes and salt antagonists. Salt substitutes are useful for persons who, for health reasons, must restrict their intake of sodium, for example, individuals suffering from hypertensions. Salt antagonists can be used, for example, to mask undesirable salty tastes in food and medicines.

Such substances can be easily identified by screening for their influence upon the function of ENAC utilizing the cloned ENAC, or the newly discovered alternatively spliced ENAC, whether transfected transiently or stably into cell lines or incorporated into membranes. By measuring the ability of test substance to stimulate or inhibit transport of sodium or its analogs by ENAC, one can identify useful substances.

EXAMPLE 1

This example shows the expression of ENAC protein in Xenopus oocytes and that expression of ENAC protein confers sodium channel activity to Xenopus oocytes.

Preparation of Expression Construct

An expression construct is prepared by ligating the coding sequence of ENAC cDNA between the 5' and 3' untranslated flanking sequences of the Xenopus β-globin cDNA. Conventional molecular genetic techniques are used (J. Sambrook et at., 1989, *Molecular Cloning: A Laboratory Manual*, Cold Spring Harbor Laboratory, Cold Spring Harbor, N.Y.) with commercially available restriction endonucleases and DNA ligase (Gibco BRL). Confirmation of the recombinants is made by enzymatic nucleotide sequencing (U.S. Biochemical). RNA transcripts are synthesized in vitro, and the RNA is purified as described by Yisraeli and Melton (*Methods Enzymol.*, 1989, 180:42).

Expression of ENAC in Xenopus Oocytes

Oocytes are removed from female *Xenopus laevis* frogs and prepared as described by Dascal (*CRC Crit. Rev. Biochem.*, 1987, 22:317–373). Oocytes are injected with 0.05 microliters of water (control) or the same volume of water containing 10 nanograms of ENAC cRNA. The oocytes are incubated for up to 96 hours at 18° C. in modified Barth's buffer (88 mM NaCl, 1 mM KCl, 0.8 mM MgSO$_4$, 0.3 mM Ca(NO$_3$)$_2$, 0.4 mM CaCl$_2$, 2.4 mM NaHCO$_3$, 10 mM HEPES, pH=7.4, total osmolality=200 m/sm/kg) also containing antibiotics. The whole oocytes are then removed and total cellular protein dissolved in 40 microliters of buffer containing 1% (w/v) SDS and analyzed by immunoblot (Towbin et al., 1979, *Proc. Natl. Acad. Sci. USA* 76:4350–4354). Expression of ENAC is monitored by immunoblot with an antibody to the ENAC.

Demonstration of Sodium Channel Activity

Xenopus oocytes express only limited sodium channel activity. Control-injected oocytes and ENAC RNA-injected oocytes are incubated at 22° C. in modified Barth's solution diluted with distilled H$_2$O to 30% of the original tonicity. Electrophysiological measurements are made 2 days after cRNA injection. Amiloride-sensitive current is measured using the two-electrode voltage-clamp technique (Palmer et al., 1990, *J. Gen. Physiology*, 96:23–46).

EXAMPLE 2

In this example, purified ENAC is reconstituted into liposomes of defined lipid composition. Sodium channel activity is then monitored.

Preparation ENAC-containing Liposomes

Neutral lipid is removed from crude *Escherichia coli* lipid (Avanti Polar Lipids, Inc.) by acetone/ether wash (Ambudkar & Maloney, 1986, *Methods. Enzymol.* 125:558–563). The purified *E. coli* bulk phospholipid is composed of phosphatidylethanolamine (70%), phosphatidylglycerol (15%), and cardiolipin (15%) (Chen & Wilson, 1984, *Proc. Natl. Acad. Sci. USA* 83:2652–2656). *E. coli* bulk phospholipid is employed since it has previously been used for functional reconstitution of several transport proteins including the glucose transporter of RBCs (Maloney & Ambudkar, 1989, *Arch. Biochem. Biophys.* 269:1–10; Chen et al., 1986, *Proc. Natl. Acad. Sci. USA* 83:2652–2656).

Highly purified ENAC protein is incorporated into proteoliposomes by detergent dilution; control liposomes are formed in an identical manner without ENAC protein.

Purified ENAC is stored overnight at 0° C. or frozen for several days at −80° C. prior to reconstitution. Reconstitution into proteoliposomes is carried out in a final volume of 1 ml containing 60–90 μg of purified ENAC protein in chromatography buffer, 9 mg of bath-sonicated *E. coli* phospholipid, 1.25% (w/v) octyl glucoside, and 50 mM Tris-HCl (pH 7.5). The mixture is briefly blended on a vortex mixer and incubated for 20 minutes on ice. Proteoliposomes (or liposomes prepared without protein) are formed at room temperature by rapidly injecting the mixture into 25 ml of buffer A [50 mM MOPS, pH 7.5, 150 mM N-methyl-D-glucamine (NMDG) chloride also containing 10–15 mM carboxyfluorescein, 1 mM dithiothreitol, and 0.5 mM PMSF]. Typically 50% (54±6%, n=5) of the ENAC protein and 70% of the phospholipid are recovered in proteoliposomes. The lipid to protein ratio is in the range of 120:1 to 219:1. These proteoliposomes have internal volumes of 1 μl/mg of phospholipid (Ambudkar and Maloney, 1986, *J. Biol. Chem.* 261:10079–10086). Protein and phospholipid are measured as described by Ambudkar & Maloney (*J. Biol. Chem.*, 1986, 261:10079–10086).

We claim:

1. An isolated α Epithelial Na Channel a comprising the amino acid sequence set forth in SEQ ID NO: 18.

2. An isolated α Epithelial Na Channel b comprising the amino acid sequence set forth in SEQ ID NO: 19.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TTATGGATGA TGGTGGCTTC                                         20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AGCACGGACG AGCCAAACCA                                       20

( 2 ) INFORMATION FOR SEQ ID NO:3:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CTCCTGGG                                                                                    8

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CAGGTSGAAT TCRYTCHTGY TYCA                                 24

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TCCAAGGAGA AGGCGCCCCC A                                                                                          21

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GAGGGCAGCC TGGATGCGG                                                                                              19

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GATCCACTCG AGNGAYTTNA CNGANGGCCA                                                                                  30

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CAGAGCTCCT GGGGCTATTG                                                                                             20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CAGAGCTCCT GGGGGCGCCT T                                                                                           21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CTTGAATTCT CTCAGAGCGC C                                                                                           21

( 2 ) INFORMATION FOR SEQ ID NO:11:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

AAGTCATTCT GCTCTGTGCG CAGTGTCAGG GACAAACCAT TGTTG    45

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CAGTTTATAA TAGCAATAGC CCAGGAGCT CTGCTTTCGG TAGTC    45

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCTGGGGAAG ATGTGCTGAA GTGAGATATC CTCAGTTTTA CAAGG    45

( 2 ) INFORMATION FOR SEQ ID NO:14:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CCTGGGGCTA TTGCTATTAT AAACTGCAGG GCGCCTTCTC CTTGGACAGC CTGGGCTGTT    60

TCTCCAAGTG TCGGAAGCCT TGTAGTGTGA TCAACTAC    98

( 2 ) INFORMATION FOR SEQ ID NO:15:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CCTGGGGGCG CCTTCTCCTT GGACAGCCTG GGCTGTCTCT CCAAGTGTCG GAAGCCTTGT    60

AGTGTGATCA ACTAC    75

( 2 ) INFORMATION FOR SEQ ID NO:16:

( i ) SEQUENCE CHARACTERISTICS:

(A) LENGTH: 19 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Rattus rattus
(F) TISSUE TYPE: taste tissue (xi) SEQUENCE DESCRIPTION: SEQ ID NO:16:

CCTGGGTGTG ACCAACTAC        19

(2) INFORMATION FOR SEQ ID NO:17:

(i) SEQUENCE CHARACTERISTICS:
(A) LENGTH: 39 amino acids
(B) TYPE: amino acid
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Rattus rattus
(F) TISSUE TYPE: taste tissue (xi) SEQUENCE DESCRIPTION: SEQ ID NO:17:

| Glu | Phe | Cys | Asp | Tyr | Arg | Lys | Gln | Ser | Ser | Trp | Gly | Tyr | Cys | Tyr | Tyr |
|---|---|---|---|---|---|---|---|---|---|---|---|---|---|---|---|
| 1 | | | | 5 | | | | | 10 | | | | | 15 | |

| Lys | Leu | Gln | Gly | Ala | Phe | Ser | Leu | Asp | Ser | Leu | Gly | Cys | Phe | Ser | Lys |
|---|---|---|---|---|---|---|---|---|---|---|---|---|---|---|---|
| | | | 20 | | | | | 25 | | | | | 30 | | |

| Cys | Arg | Lys | Pro | Cys | Ser | Val |
|---|---|---|---|---|---|---|
| | | 35 | | | | |

(2) INFORMATION FOR SEQ ID NO:18:

(i) SEQUENCE CHARACTERISTICS:
(A) LENGTH: 29 amino acids
(B) TYPE: amino acid
(D) TOPOLOGY: linear (ii) MOLECULE TYPE: protein (iii) HYPOTHETICAL: YES (iv) ANTI-SENSE: NO (v) FRAGMENT TYPE: internal (vi) ORIGINAL SOURCE:
(A) ORGANISM: Rattus rattus
(F) TISSUE TYPE: taste tissue (xi) SEQUENCE DESCRIPTION: SEQ ID NO:18:

| Glu | Phe | Cys | Asp | Tyr | Arg | Lys | Gln | Ser | Ser | Trp | Gly | Arg | Leu | Leu | Leu |
|---|---|---|---|---|---|---|---|---|---|---|---|---|---|---|---|
| 1 | | | | 5 | | | | | 10 | | | | | 15 | |

| Gly | Gln | Pro | Gly | Leu | Ser | Leu | Gln | Val | Ser | Glu | Ala | Leu |
|---|---|---|---|---|---|---|---|---|---|---|---|---|
| | | | 20 | | | | | 25 | | | | |

(2) INFORMATION FOR SEQ ID NO:19:

(i) SEQUENCE CHARACTERISTICS:

(A) LENGTH: 12 amino acids
(B) TYPE: amino acid
(D) TOPOLOGY: linear (ii) MOLECULE TYPE: protein (iii) HYPOTHETICAL: YES (iv) ANTI-SENSE: NO (v) FRAGMENT TYPE: internal (vi) ORIGINAL SOURCE:
(A) ORGANISM: Rattus rattus
(F) TISSUE TYPE: taste tissue (xi) SEQUENCE DESCRIPTION: SEQ ID NO:19:

```
Glu Phe Cys Asp Tyr Arg Lys Gln Ser Ser Trp Val
1               5                   10
```

(2) INFORMATION FOR SEQ ID NO:20:

(i) SEQUENCE CHARACTERISTICS:
(A) LENGTH: 698 amino acids
(B) TYPE: amino acid
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Rattus rattus (xi) SEQUENCE DESCRIPTION: SEQ ID NO:20:

```
Met Leu Asp His Thr Arg Ala Pro Glu Leu Asn Ile Asp Leu Asp Leu
1               5                   10                  15

His Ala Ser Asn Ser Pro Lys Gly Ser Met Lys Gly Asn Gln Phe Lys
                20                  25                  30

Glu Gln Asp Pro Cys Pro Pro Gln Pro Met Gln Gly Leu Gly Lys Gly
            35                  40                  45

Asp Lys Arg Glu Glu Gln Gly Leu Gly Pro Glu Pro Ser Ala Pro Arg
        50                  55                  60

Gln Pro Thr Glu Glu Glu Glu Ala Leu Ile Glu Phe His Arg Ser Tyr
65                  70                  75                  80

Arg Glu Leu Phe Gln Phe Phe Cys Asn Asn Thr Thr Ile His Gly Ala
                85                  90                  95

Ile Arg Leu Val Cys Ser Lys His Asn Arg Met Lys Thr Ala Phe Trp
                100             105                 110

Ala Val Leu Trp Leu Cys Thr Phe Gly Met Met Tyr Trp Gln Phe Ala
            115                 120                 125

Leu Leu Phe Glu Glu Tyr Leu Ser Tyr Pro Val Ser Leu Asn Ile Asn
    130                 135                 140

Leu Asn Ser Asp Lys Leu Val Phe Pro Ala Val Thr Val Cys Thr Leu
145                 150                 155                 160

Asn Pro Tyr Arg Tyr Thr Glu Ile Lys Glu Glu Leu Glu Glu Leu Asp
                165                 170                 175

Arg Ile Thr Glu Gln Thr Leu Phe Asp Leu Tyr Lys Tyr Asn Ser Ser
            180                 185                 190

Tyr Thr Arg Gln Ala Gly Ala Arg Arg Arg Ser Ser Arg Asp Leu Leu
        195                 200                 205

Gly Ala Phe Pro His Pro Leu Gln Arg Leu Arg Thr Pro Pro Pro Pro
```

```
              210                    215                     220
Tyr   Ser   Gly   Arg   Thr   Ala   Arg   Ser   Gly   Ser   Ser   Ser   Val   Arg   Asp   Asn
225                     230                     235                                 240

Asn   Pro   Gln   Val   Asp   Arg   Lys   Asp   Trp   Lys   Ile   Gly   Phe   Gln   Leu   Cys
                        245                     250                           255

Asn   Gln   Asn   Lys   Ser   Asp   Cys   Phe   Tyr   Gln   Thr   Tyr   Ser   Ser   Gly   Val
                  260                     265                           270

Asp   Ala   Val   Arg   Glu   Trp   Tyr   Arg   Phe   His   Tyr   Ile   Asn   Ile   Leu   Ser
                  275                     280                           285

Arg   Leu   Ser   Asp   Thr   Ser   Pro   Ala   Leu   Glu   Glu   Ala   Leu   Gly   Asn
      290                     295                           300

Phe   Ile   Phe   Thr   Cys   Arg   Phe   Asn   Gln   Ala   Pro   Cys   Asn   Gln   Ala   Asn
305                           310                     315                                 320

Tyr   Ser   Lys   Phe   His   His   Pro   Met   Tyr   Gly   Asn   Cys   Tyr   Thr   Phe   Asn
                        325                     330                           335

Asp   Lys   Asn   Asn   Ser   Asn   Leu   Trp   Met   Ser   Ser   Met   Pro   Gly   Val   Asn
                  340                     345                           350

Asn   Gly   Leu   Ser   Leu   Thr   Leu   Arg   Thr   Glu   Gln   Asn   Asp   Phe   Ile   Pro
                  355                     360                           365

Leu   Leu   Ser   Thr   Val   Thr   Gly   Ala   Arg   Val   Met   Val   His   Gly   Gln   Asp
      370                     375                           380

Glu   Pro   Ala   Phe   Met   Asp   Asp   Gly   Gly   Phe   Asn   Leu   Arg   Pro   Gly   Val
385                           390                     395                                 400

Glu   Thr   Ser   Ile   Ser   Met   Arg   Lys   Glu   Ala   Leu   Asp   Ser   Leu   Gly   Gly
                        405                     410                           415

Asn   Tyr   Gly   Asp   Cys   Thr   Glu   Asn   Gly   Ser   Asp   Val   Pro   Val   Lys   Asn
                  420                     425                           430

Leu   Tyr   Pro   Ser   Lys   Tyr   Thr   Gln   Gln   Val   Cys   Ile   His   Ser   Cys   Phe
                  435                     440                           445

Gln   Glu   Asn   Met   Ile   Lys   Lys   Cys   Gly   Cys   Ala   Tyr   Ile   Phe   Tyr   Pro
      450                     455                           460

Lys   Pro   Lys   Gly   Val   Glu   Phe   Cys   Asp   Tyr   Arg   Lys   Gln   Ser   Ser   Trp
465                           470                     475                                 480

Gly   Tyr   Cys   Tyr   Tyr   Lys   Leu   Gln   Gly   Ala   Phe   Ser   Leu   Asp   Ser   Leu
                        485                     490                           495

Gly   Cys   Phe   Ser   Lys   Cys   Arg   Lys   Pro   Cys   Ser   Val   Ile   Asn   Tyr   Lys
                  500                     505                           510

Leu   Ser   Ala   Gly   Tyr   Ser   Arg   Trp   Pro   Ser   Val   Lys   Ser   Gln   Asp   Trp
                  515                     520                           525

Ile   Phe   Glu   Met   Leu   Ser   Leu   Gln   Asn   Asn   Tyr   Thr   Ile   Asn   Asn   Lys
      530                     535                           540

Arg   Asn   Gly   Val   Ala   Lys   Leu   Asn   Ile   Phe   Phe   Lys   Glu   Leu   Asn   Tyr
545                           550                     555                                 560

Lys   Thr   Asn   Ser   Glu   Ser   Pro   Ser   Val   Thr   Met   Val   Ser   Leu   Leu   Ser
                        565                     570                           575

Asn   Leu   Gly   Ser   Gln   Trp   Ser   Leu   Trp   Phe   Gly   Ser   Ser   Val   Leu   Ser
                  580                     585                           590

Val   Val   Glu   Met   Ala   Asp   Val   Ile   Phe   Asp   Leu   Leu   Val   Ile   Thr   Leu
                  595                     600                           605

Leu   Met   Leu   Leu   Arg   Arg   Phe   Arg   Ser   Arg   Tyr   Trp   Ser   Pro   Gly   Arg
      610                     615                           620

Gly   Ala   Arg   Gly   Ala   Arg   Glu   Val   Ala   Ser   Thr   Pro   Ala   Ser   Ser   Phe
625                           630                     635                                 640
```

-continued

| | | | | | | | | | | | | | |
|---|---|---|---|---|---|---|---|---|---|---|---|---|---|
| Pro | Ser | Arg | Phe 645 | Cys | Pro | His | Pro | Thr 650 | Ser | Pro | Pro | Ser 655 | Leu | Pro |
| Gln | Gln | Gly | Met 660 | Thr | Pro | Pro | Leu 665 | Ala | Leu | Thr | Ala | Pro 670 | Pro | Pro | Ala |
| Tyr | Ala | Thr 675 | Leu | Gly | Pro | Ser | Ala 680 | Pro | Pro | Leu | Asp | Ser 685 | Ala | Ala | Pro |
| Asp | Cys 690 | Ser | Ala | Cys | Ala | Leu 695 | Ala | Ala | Leu | | | | |